United States Patent
Raksi

(10) Patent No.: US 10,182,943 B2
(45) Date of Patent: *Jan. 22, 2019

(54) ADJUSTABLE PUPIL SYSTEM FOR SURGICAL LASER SYSTEMS

(75) Inventor: Ferenc Raksi, Mission Viejo, CA (US)

(73) Assignee: ALCON LENSX, INC.

( * ) Notice: Subject to any disclaimer, the term of this patent is extended or adjusted under 35 U.S.C. 154(b) by 2085 days.

This patent is subject to a terminal disclaimer.

(21) Appl. No.: 13/416,255

(22) Filed: Mar. 9, 2012

(65) Prior Publication Data
US 2013/0237972 A1   Sep. 12, 2013

Related U.S. Application Data

(63) Continuation-in-part of application No. 13/416,123, filed on Mar. 9, 2012, now Pat. No. 8,852,177.

(51) Int. Cl.
A61F 9/011   (2006.01)
A61F 9/008   (2006.01)

(52) U.S. Cl.
CPC ........ *A61F 9/0084* (2013.01); *A61F 9/00825* (2013.01); *A61F 2009/0087* (2013.01); *A61F 2009/00887* (2013.01); *A61F 2009/00897* (2013.01)

(58) Field of Classification Search
CPC .............. A61F 9/00825; A61F 9/0084; A61F 2009/0087; A61F 2009/00887; A61F 2009/00897
USPC ............................................. 606/4, 5, 10–14
See application file for complete search history.

(56) References Cited

U.S. PATENT DOCUMENTS

| 4,538,608 A * | 9/1985 | L'Esperance, Jr. ......................... A61F 9/00736 372/24 |
| 4,579,430 A * | 4/1986 | Bille .................... A61B 3/1015 351/206 |
| 4,635,299 A | 1/1987 | MacGovern |
| 4,729,372 A * | 3/1988 | L'Esperance, Jr. ......................... A61F 9/00804 219/121.67 |

(Continued)

FOREIGN PATENT DOCUMENTS

| EP | 0326760 | 8/1989 |
| EP | 1279386 | 1/2003 |

(Continued)

OTHER PUBLICATIONS

PCT International Search Report for corresponding International Application No. PCT/US2013/029883, dated Jun. 25, 2013, 3 pages.

(Continued)

*Primary Examiner* — David Shay
(74) *Attorney, Agent, or Firm* — Keiko Ichiye, Esq.

(57) ABSTRACT

A surgical laser system can include a laser engine to generate a laser beam of laser pulses, a scanning delivery system to direct the laser beam to a target region and to scan the laser beam along a scan-pattern in the target region, and a pupil system to modulate the laser beam. In addition, a method of adjusting a pupil of a laser beam can include: generating a laser beam of laser pulses with a laser engine, directing the laser beam to a target region with a scanning delivery system, scanning the laser beam along a scan-pattern in the target region with the scanning delivery system, and performing a modulation of the laser beam with an adjustable pupil system.

11 Claims, 23 Drawing Sheets

(56) References Cited

U.S. PATENT DOCUMENTS

| | | | |
|---|---|---|---|
| 4,901,718 A * | 2/1990 | Bille | A61B 18/20 606/18 |
| 5,541,951 A | 7/1996 | Juhasz et al. | |
| 5,548,234 A | 8/1996 | Turi et al. | |
| 5,549,632 A | 8/1996 | Lai | |
| 5,561,678 A | 10/1996 | Juhasz et al. | |
| 5,656,186 A | 8/1997 | Mourou et al. | |
| 5,789,734 A | 8/1998 | Torigoe et al. | |
| 6,081,543 A | 6/2000 | Liu et al. | |
| 6,099,522 A | 8/2000 | Knopp et al. | |
| 6,203,539 B1 | 3/2001 | Shimmick et al. | |
| 6,220,707 B1 | 4/2001 | Bille | |
| 6,324,191 B1 | 11/2001 | Horvath | |
| 6,610,050 B2 | 8/2003 | Bille | |
| 6,610,051 B2 | 8/2003 | Bille | |
| 6,693,927 B1 | 2/2004 | Horvath et al. | |
| 6,726,680 B1 | 4/2004 | Knopp et al. | |
| 6,746,121 B2 | 6/2004 | Ross et al. | |
| 6,751,033 B2 | 6/2004 | Goldstein et al. | |
| 6,908,196 B2 | 6/2005 | Herekar et al. | |
| 6,992,765 B2 | 1/2006 | Horvath et al. | |
| 7,027,233 B2 | 4/2006 | Goldstein et al. | |
| 7,131,968 B2 | 11/2006 | Bendett et al. | |
| 7,145,661 B2 | 12/2006 | Hitzenberger | |
| 7,330,275 B2 | 2/2008 | Raksi | |
| 7,336,366 B2 | 2/2008 | Choma | |
| 7,390,089 B2 | 6/2008 | Loesel et al. | |
| 7,452,080 B2 | 11/2008 | Wiltberger et al. | |
| 7,452,081 B2 | 11/2008 | Wiltberger et al. | |
| 7,522,642 B2 | 4/2009 | Zadoyan et al. | |
| 7,584,756 B2 | 9/2009 | Zadoyan et al. | |
| 7,597,444 B2 | 10/2009 | Rathjen et al. | |
| 7,599,591 B2 | 10/2009 | Andersen et al. | |
| 7,655,002 B2 | 2/2010 | Myers | |
| 7,918,559 B2 | 4/2011 | Tesar | |
| 8,246,609 B2 | 8/2012 | Zickler et al. | |
| 8,262,646 B2 | 9/2012 | Frey et al. | |
| 2003/0053219 A1 | 3/2003 | Manzi | |
| 2004/0059321 A1 | 3/2004 | Knopp et al. | |
| 2004/0202351 A1 | 10/2004 | Park et al. | |
| 2004/0243112 A1 | 12/2004 | Bendett et al. | |
| 2004/0254568 A1 | 12/2004 | Rathjen | |
| 2005/0228366 A1 | 10/2005 | Kessler et al. | |
| 2006/0084954 A1 | 4/2006 | Zadoyan et al. | |
| 2006/0100613 A1 | 5/2006 | McArdle et al. | |
| 2006/0195076 A1 | 8/2006 | Blumenkranz et al. | |
| 2007/0106285 A1 | 5/2007 | Raksi | |
| 2007/0121069 A1 | 5/2007 | Andersen et al. | |
| 2007/0126985 A1 | 6/2007 | Wiltberger et al. | |
| 2007/0129709 A1 | 6/2007 | Andersen et al. | |
| 2007/0129775 A1 | 6/2007 | Mordaunt et al. | |
| 2007/0173791 A1 | 7/2007 | Raksi | |
| 2007/0173795 A1 | 7/2007 | Frey et al. | |
| 2007/0173796 A1 | 7/2007 | Kessler et al. | |
| 2007/0185475 A1 | 8/2007 | Frey et al. | |
| 2007/0219541 A1 | 9/2007 | Kurtz | |
| 2007/0235543 A1 | 10/2007 | Zadoyan et al. | |
| 2007/0282313 A1 | 12/2007 | Huang et al. | |
| 2008/0015553 A1 | 1/2008 | Zacharias | |
| 2008/0033406 A1 | 2/2008 | Andersen et al. | |
| 2008/0077121 A1 | 3/2008 | Rathjen | |
| 2008/0147052 A1 | 6/2008 | Bendett et al. | |
| 2008/0167642 A1 | 7/2008 | Palanker et al. | |
| 2008/0192783 A1 | 8/2008 | Rathjen et al. | |
| 2008/0228176 A1 | 9/2008 | Triebel et al. | |
| 2008/0231807 A1 | 9/2008 | Lacombe et al. | |
| 2008/0269731 A1 | 10/2008 | Swinger et al. | |
| 2008/0281303 A1 | 11/2008 | Culbertson et al. | |
| 2008/0319428 A1 | 12/2008 | Wiechmann et al. | |
| 2008/0319464 A1 | 12/2008 | Bischoff et al. | |
| 2009/0002835 A1 | 1/2009 | Prior et al. | |
| 2009/0012507 A1 | 1/2009 | Culbertson et al. | |
| 2009/0118718 A1 | 5/2009 | Raksi et al. | |
| 2009/0131921 A1 | 5/2009 | Kurtz et al. | |
| 2009/0149841 A1 | 6/2009 | Kurtz | |
| 2009/0171327 A1 | 7/2009 | Kurtz et al. | |
| 2009/0231704 A1 | 9/2009 | Chen | |
| 2009/0296083 A1 | 12/2009 | Saaski et al. | |
| 2009/0299347 A1 | 12/2009 | Vogler et al. | |
| 2010/0004641 A1 | 1/2010 | Frey et al. | |
| 2010/0042079 A1 | 2/2010 | Frey et al. | |
| 2010/0082017 A1 | 4/2010 | Zickler et al. | |
| 2010/0130966 A1 | 5/2010 | Brownell | |
| 2010/0191226 A1 | 7/2010 | Blumenkranz et al. | |
| 2011/0034911 A1 | 2/2011 | Bischoff et al. | |
| 2011/0184392 A1 | 7/2011 | Culbertson et al. | |
| 2011/0205492 A1 | 8/2011 | Rathjen | |
| 2011/0264081 A1 | 10/2011 | Reich et al. | |

FOREIGN PATENT DOCUMENTS

| | | |
|---|---|---|
| EP | 1584310 | 10/2005 |
| WO | 98/56298 | 12/1998 |
| WO | 2007/021022 | 2/2007 |
| WO | 2007/056486 | 5/2007 |
| WO | 2008/055506 | 5/2008 |
| WO | 2009/089504 | 7/2009 |

OTHER PUBLICATIONS

An, Lin and Wang, Ruikang K., "Use of a scanner to modulate spatial interferograms for in vivo full-range Fourier-domain optical coherence tomography", Dec. 1, 2007, Optics Letters, vol. 32(23); pp. 3423-3425.

European Supplementary European Search Report for EP Application No. 10806836.2 dated Oct. 8, 2012, 4 pages.

Duma et al., "Determination of Significant Parameters for Eye Injury Risk from Projectiles", Oct. 2005; Journal of Trauma Injury, Infection, and Critical Care, 59(4):960-4, 5 pages.

Gwon et al., "Focal laser photophacoablation of normal and cataractous lenses in rabbits: Preliminary report," May 1995, J. Cataract Refract Surg, 21:282-286, 5 pages.

Kruger et al., "Experimental Increase in Accommodative Potential after Neodymium: Yttrium-Aluminum-Garnet Laser," Jun. 2001, Ophthalmology 108:2122-2129, 8 pages.

Ryan et al., "Nd:YAG Laser Photodisruption of the Lens Nucleus Before Phacoemulsification," Oct. 1987, American Journal of Ophthalmology 104:382-386, 5 pages.

* cited by examiner

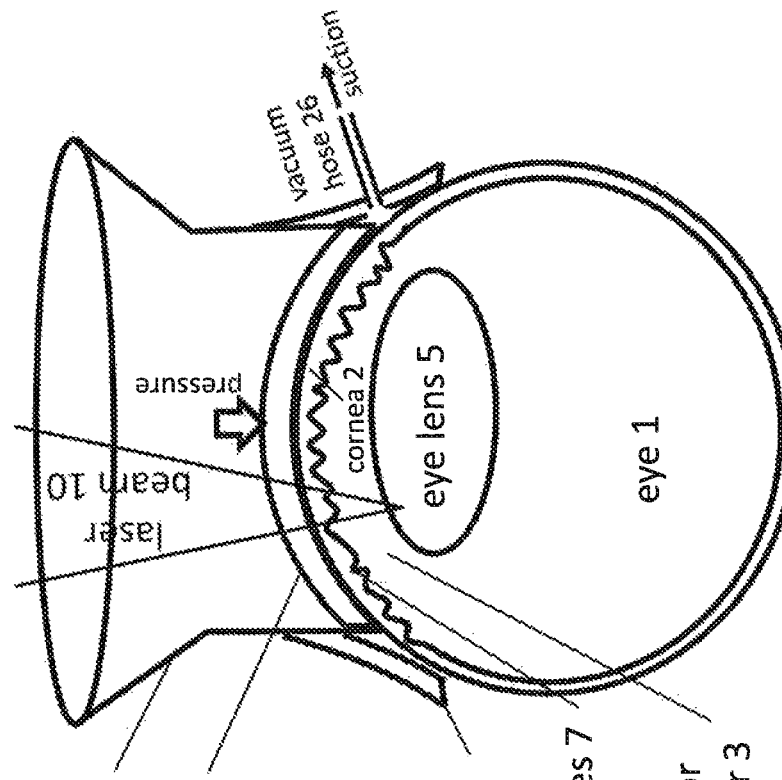
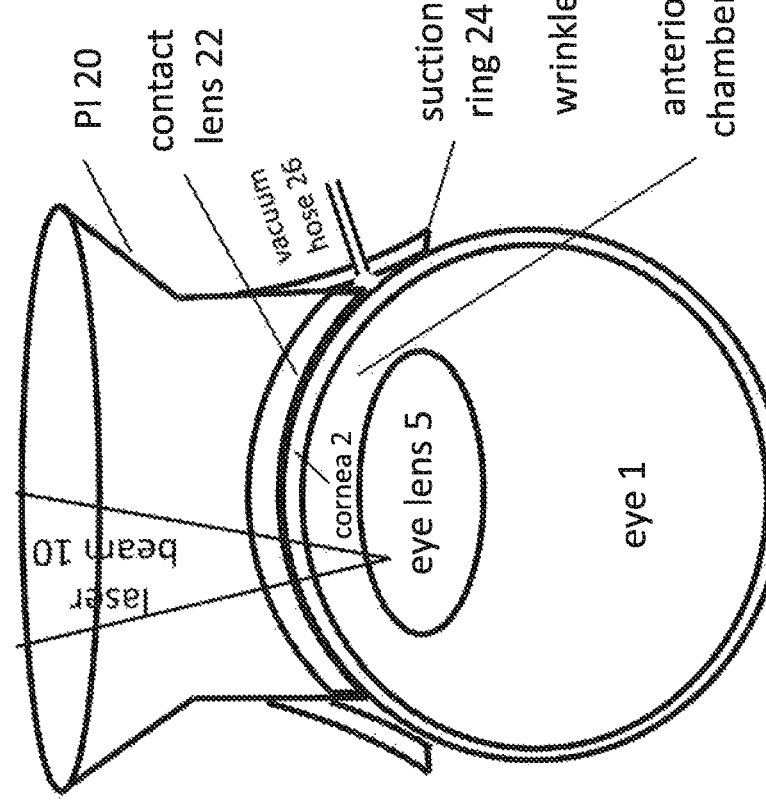

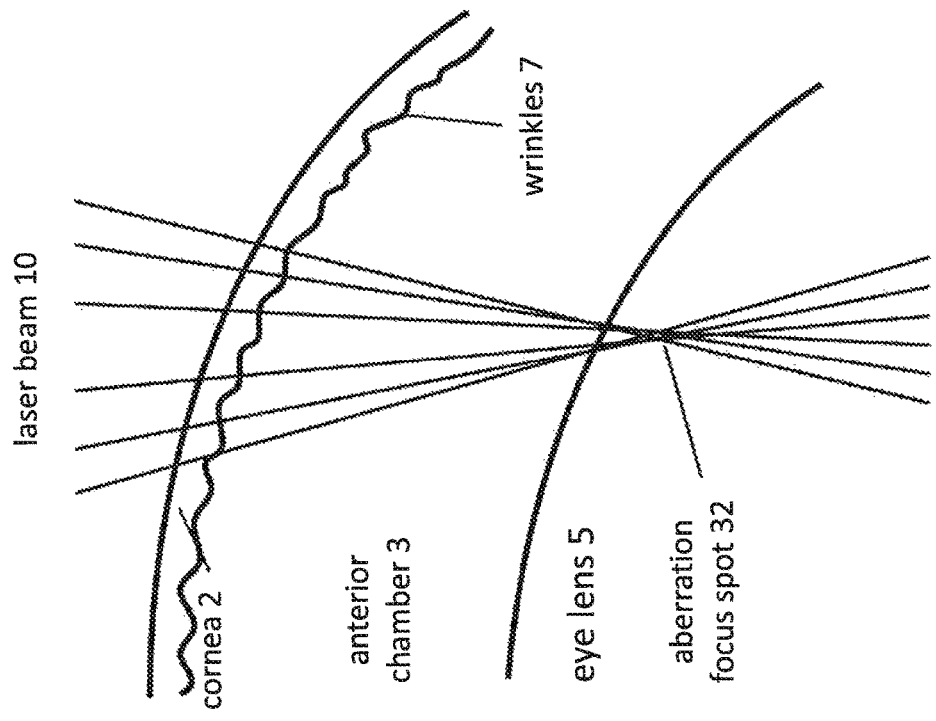
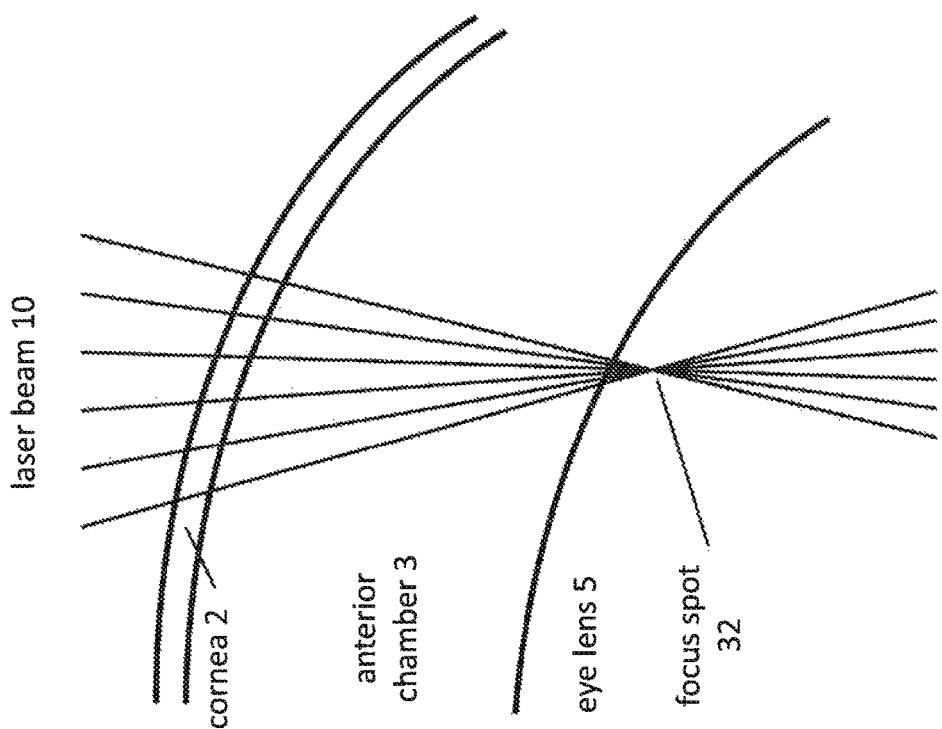
FIG. 2B
FIG. 2A

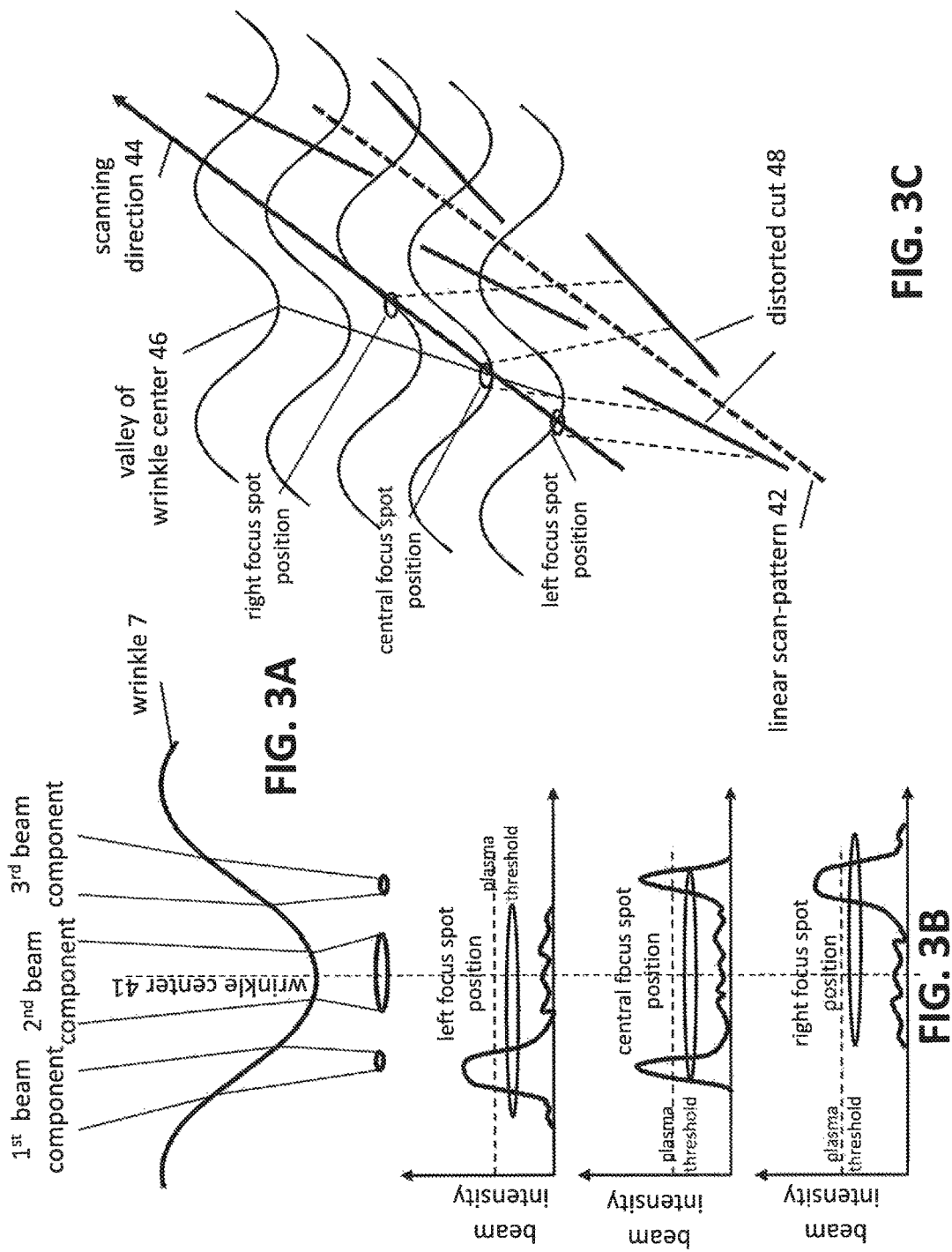

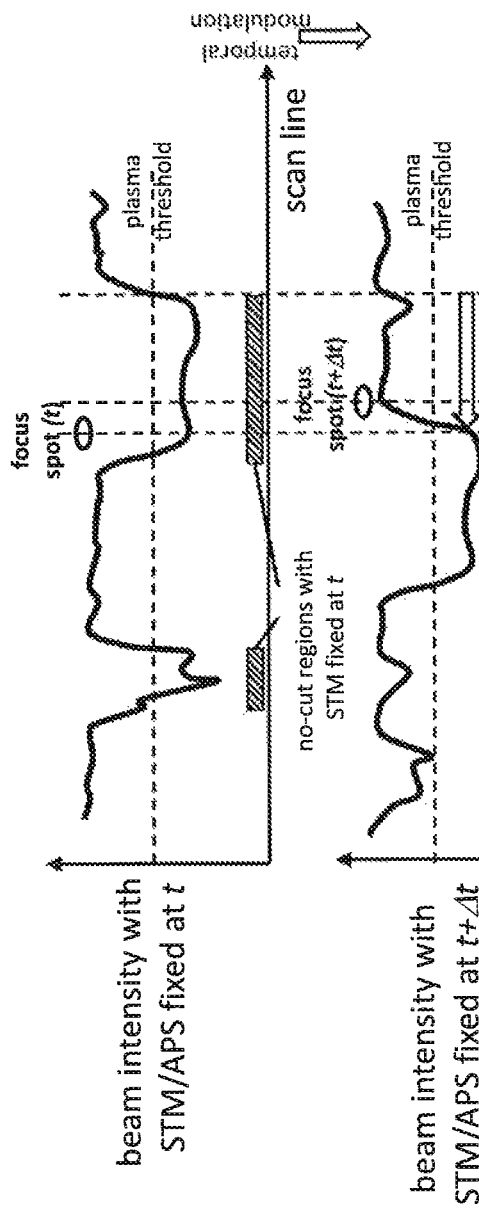
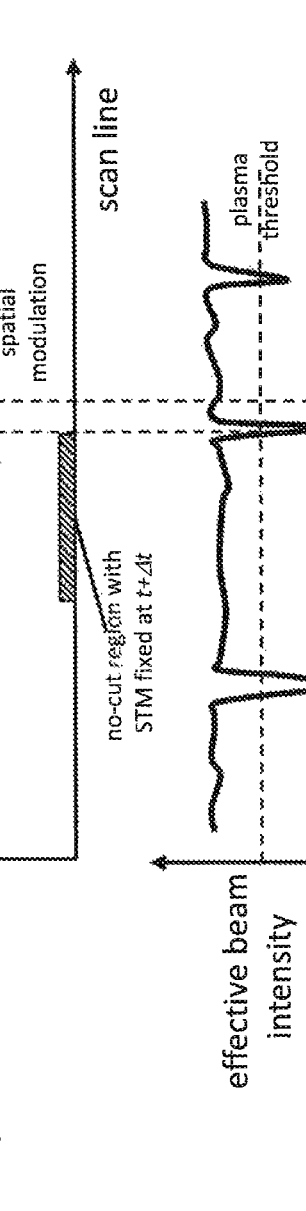
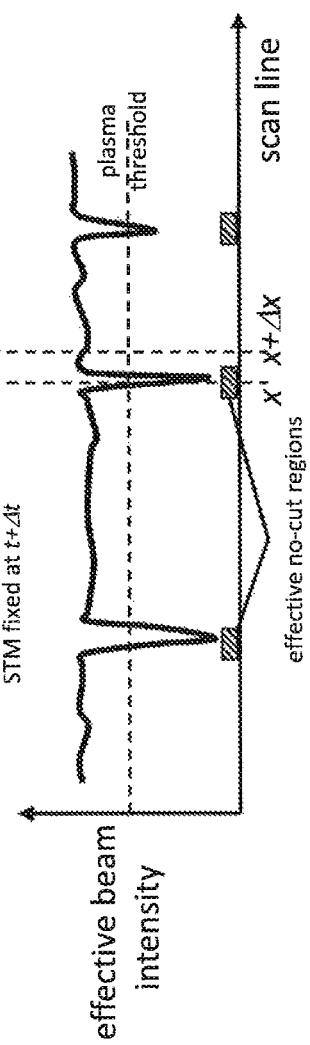
FIG. 6A
FIG. 6B
FIG. 6C

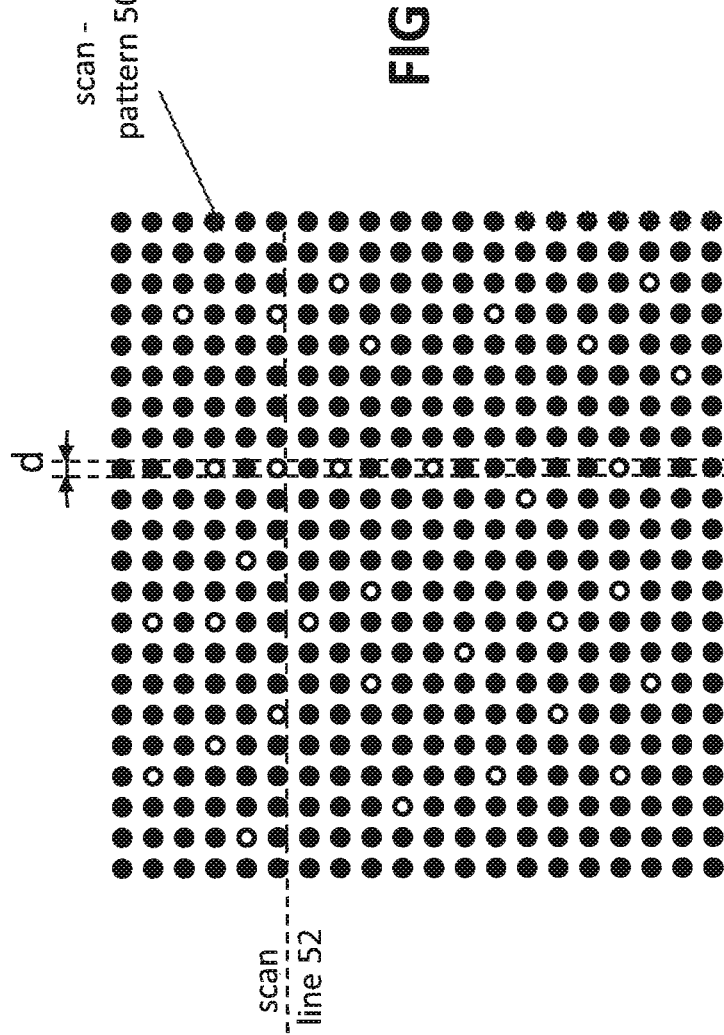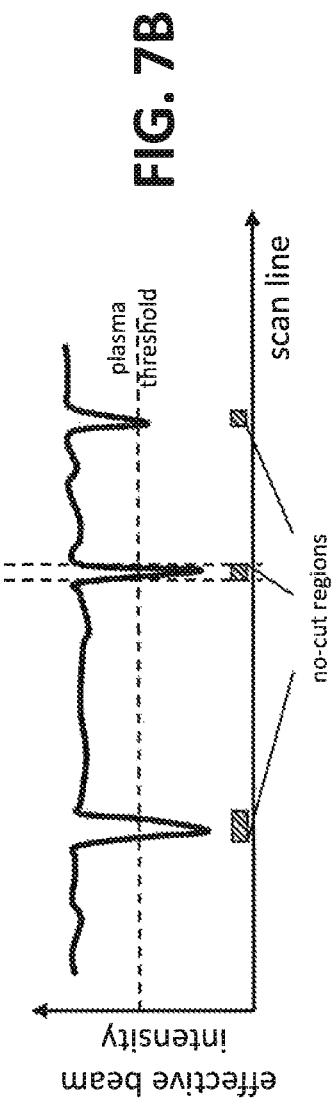
FIG. 7A
FIG. 7B

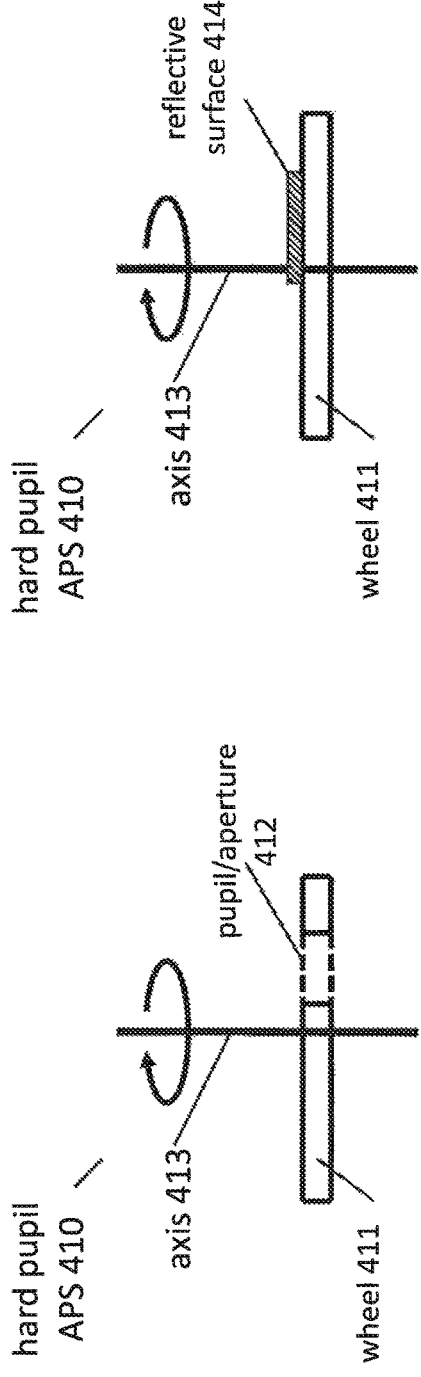
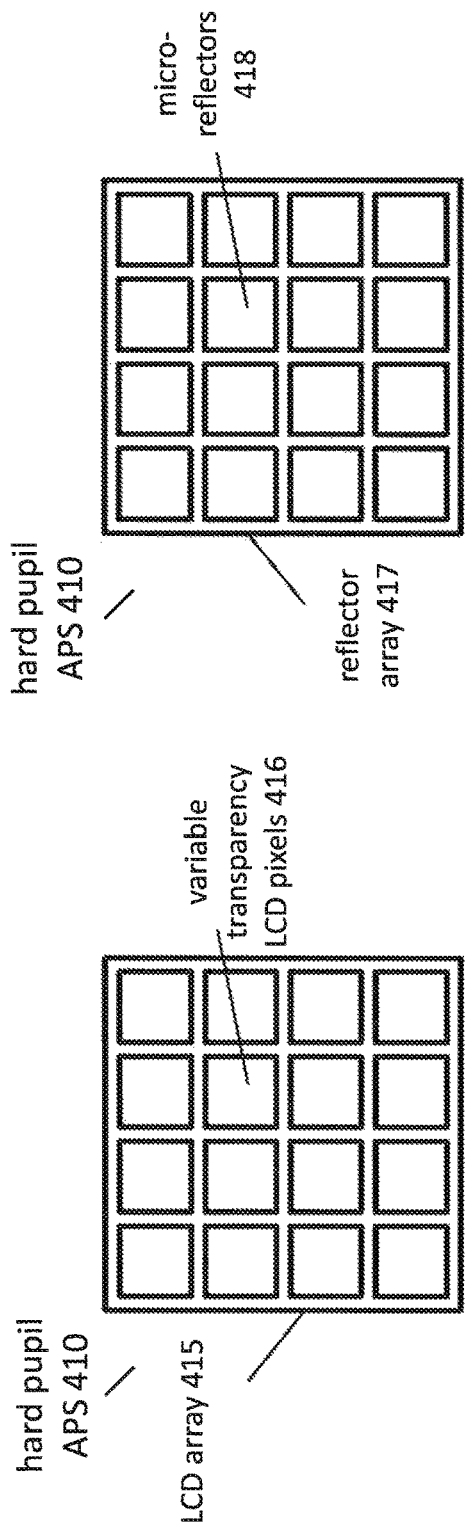
FIG. 13A
FIG. 13B
FIG. 13C
FIG. 13D

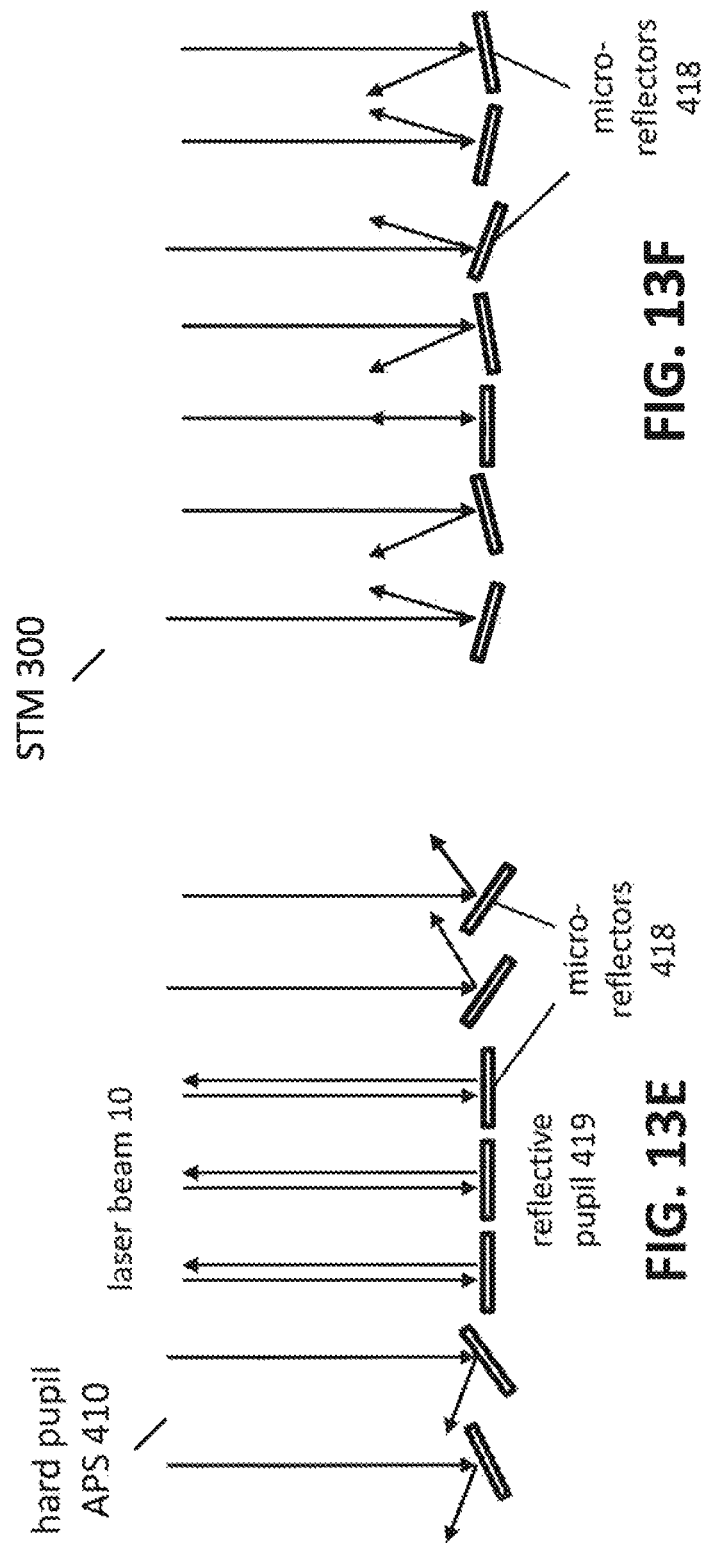

ADJUSTABLE PUPIL SYSTEM FOR SURGICAL LASER SYSTEMS

CROSS REFERENCE TO RELATED APPLICATION

This application is a continuation-in-part of the patent application entitled "Spatio-Temporal Beam Modulator for Surgical Laser Systems" by the same inventor, filed on the same day, with U.S. application Ser. No. 13/416,123.

TECHNICAL FIELD

This patent document relates to surgical laser systems. More precisely, this patent document relates to homogenizing a laser beam by a spatio-temporal beam modulator in ophthalmic surgical laser systems.

BACKGROUND

Surgery with femtosecond ophthalmic lasers is based on generating a pulsed laser beam and delivering the laser pulses by a scanning delivery system through a focusing optics to a sequence of focus spots along a scan-pattern in a target region of an ophthalmic tissue. Each laser pulse creates a plasma or cavitation bubble in the target tissue at the focus spot of the laser beam when the beam intensity or energy density exceeds a plasma or photodisruption threshold. During surgery, the focus spot of the laser beam is scanned along a three dimensional scan-pattern, creating a sequence of these bubbles to form macroscopic surgical cuts or photodisrupted regions.

During the surgery, however, the laser beam can also cause unintended collateral damage away from the focus spot such as excessive heating and shock-waves in the target tissue and light poisoning in the retina. Therefore, surgical systems are designed to deliver the laser beam with an energy density that exceeds the photodisruption threshold, but only marginally to achieve the surgical functionality while minimizing the collateral damage.

The energy density or beam intensity is determined by the energy, duration and repetition rate of the individual laser pulses and the size of the focus spot. Modern surgical laser systems provide high precision and control by using precisely controlled laser sources, refined optical designs, high quality optical parts and an objective with a large numerical aperture to focus the laser beam down to a diffraction limited focus spot with a diameter of a few microns, and do so at all points of the scan-pattern within a surgical volume, or at all scanner positions of the surgical laser system. This high precision makes the modern laser surgical systems capable of maintaining the beam intensity marginally above the plasma threshold along the entire scan-pattern within the surgical volume in ideal or model targets.

Unfortunately, in spite of all the design and manufacturing effort spent on optimizing the laser sources and optics, the focus spot in the ophthalmic target region is often still larger than its diffraction limited value because the target tissue itself often gets distorted, making it different from the ideal or model targets used during the design of the laser optics. Distortions can be also caused by imperfections of the scanning delivery system and the focusing optics. The enlarging of the focus spot caused by any of these distortions can lead to failing surgical performance since it lowers the pulse energy density or beam intensity below the plasma threshold and thus prevents the scanning laser beam from forming the planned surgical cuts, leaving uncut lines or regions in the target region.

This problem of failing surgical performance can become particularly acute during surgical cuts where the targeted tissue is very thin such as a capsulotomy of the thin lens capsular bag during a cataract surgery. Since the targeted tissue is thin, the laser beam scans it only once or only a few times along a loop, as this scan-pattern should be already capable of cutting through the entire thickness of the capsular bag. However, if any one of the above distortions reduces the beam intensity below the plasma threshold along a section of the loop then that section can remain uncut. This uncut section of the capsular bag needs to be cut and separated manually, possibly leading to a tearing of the capsular bag and thus to a substantial lowering of the precision of the cataract surgery. Therefore, there is a need for surgical laser systems that can deliver the laser beam with a pulse energy density that is marginally higher than the plasma threshold in the entire surgical volume even if distortions are present along the beam path either in the target region or in the optical system itself, as such laser systems are capable of cutting the target region according to the scan-pattern in the entire surgical volume without leaving uncut regions or lines.

SUMMARY

An objective of cataract surgery is to direct or deliver a surgical laser beam 10 into an eye 1 through its cornea 2 and anterior chamber 3 to photodisrupt a cataractous target region in a lens 5. FIGS. 1A-E illustrate some of the problems caused by beam distortions in cataract surgery. FIG. 1A illustrates that many surgical laser systems have a patient interface (PI) 20 attached to a distal end of an objective of the laser scanning delivery system. The PI 20 can include a contact lens 22 that makes contact with the cornea 2 to allow a well-controlled entry of the surgical laser beam 10 into the cornea 2. The PI 20 is often outfitted with a suction ring 24 and a vacuum hose 26 for creating a reliable mechanical coupling with the eye 1.

FIG. 1B illustrates that the PI 20 and its contact lens 22 can be coupled to the cornea 2 reliably by applying suction to the vacuum hose 26 that presses the contact lens 22 to the cornea 2. Sometimes, the PI 20 and its contact lens 22 can be additionally pressed against the cornea 2 by its own weight or by a mechanical system such as spring loading.

FIG. 1B also shows that, unfortunately, the pressure caused by the vacuum suction and the mechanical pressure can create wrinkles 7 in the cornea 2 which can cause the above mentioned beam distortions.

FIG. 1C illustrates a mathematical formulation of the distortions or aberrations of the laser beam 10. It is customary to define an aberration as the deviation of a wavefront of the laser beam 10 from a conceptual Gaussian reference sphere segment S of radius R. The Gaussian sphere segment S can be centered on the geometrical focal point $P_0$ of the laser beam 10 and formed by the intersection of the laser beam 10 and an entire Gaussian reference sphere. In many cases, the reference sphere segment S is the pupil of the laser system. The two main classes of distortions or aberrations are phase and amplitude distortions/aberrations. The formulation is presented here for the more typical phase aberrations. Amplitude aberrations can be described in an analogous manner.

It is known from the theory of optical wave propagation that the intensity of light I(P) at a point P in the focal plane that contains the geometrical focus point $P_0$ is given by the absolute value squared of the electromagnetic disturbance, in essence the electric field, with the fast oscillating $e^{i\omega t}$ factor removed:

$$I(P)=|U(P)|^2.$$

According to the Huygens-Fresnel principle, the electric field U(P) at the point P is given by an integral of the beam components E(Q,P) over the Gaussian reference sphere segment S:

$$U(P) = -\frac{i}{\lambda}\int\int_S E(Q,P)dS(Q) =$$
$$-\frac{i}{\lambda}\int\int_S E_0(Q,P)e^{ik\Phi}dS(Q) = -\frac{i}{\lambda}\int\int_S A\frac{e^{ik(s-R)}e^{ik\Phi}}{sR}dS(Q)$$

Here, E(Q,P) is the propagating electric field, or beam component that propagates from a dS(Q) vicinity of point Q on the Gaussian reference sphere segment S to the point P of the focal plane near $P_0$, the geometrical focus point. This beam component can be decomposed into $E_0(Q,P)$, the propagating electric field in the absence of a phase aberration and into $e^{ik\Phi}$, representing the phase aberration by a phase aberration function $\Phi$. The undistorted field can be represented as:

$$E_0(Q,P) = A\frac{e^{ik(s-R)}}{Rs}.$$

Here, A is the amplitude of the beam component at point Q, reduced during the propagation to point P by 1/s, where s is the length of the QP ray from the point Q to point P. Further, $e^{ik(s-R)}$ represents the propagating wave phase factor, acquired by the propagating electromagnetic wave $E_0(Q,P)$ in the absence of aberrations. Finally, $k=2\pi/\lambda$ is the wavenumber and $\lambda$ is the wavelength of the laser beam 10. Discussing the aberration-free beam, for $P=P_0$ s=R and thus the phase factors of the beam components that propagate from the different Q points of the reference sphere segment S to the geometrical focus point $P_0$ add up with maximum constructive interference. Further, as known, the interference remains constructive in a small but finite vicinity of the geometrical focus point $P_0$, broadening the geometrical focus point $P_0$ into a diffraction limited focus spot 32.

FIG. 1D illustrates the beam intensity along a typical scan line in the target region when the laser beam is scanned over an unwrinkled cornea. Since the aberration function is essentially zero in this region, the propagating wave phase factors $e^{ik(s-R)}$ of the beam components E(Q,P) in the Huygens-Fresnel integral can add smoothly and constructively when reaching P points in the vicinity the geometrical focus point $P_0$, thus producing a laser beam 10 with a beam intensity that can remain above the plasma threshold along the shown and the other scan lines within the surgical volume. Therefore, as the laser beam 10 is scanned across the scan lines of the scan-pattern, it can create the intended surgical cuts in the entire surgical volume.

FIG. 1E illustrates that, in contrast to the unwrinkled case of FIG. 1D, if the vacuum suction or the mechanical pressure creates corneal wrinkles 7, then these wrinkles 7 can distort the laser, beam 10 by refracting the propagating electric fields, or beam components, to distorted directions, so that their aberration function $\Phi$ in the Huygens-Fresnel integral become different from zero. The corresponding phase factors $e^{ik\Phi}$ can lead to a substantially destructive interference between the beam components, possibly substantially reducing the beam intensity. The magnitude of the corneal phase aberration can be estimated as the product of the amplitude of the wrinkles and the change of the refractive index at the cornea-aqueous humor interface. The refractive index of the cornea is approximately 1.377 while the index of the aqueous humor is 1.337, separated by a difference of 0.04. As an example, for a laser wavelength of 1 micrometer, wrinkles with amplitude of 25 micrometers give approximately $2\pi$ phase aberration. Therefore, in general, for $\Phi > \pi/4$ the phase aberrations can already substantially reduce the beam intensity, and for $\Phi > \pi/2$ the aberrations even reverse the sign of the contributions of the beam components E(Q,P) to the Huygens-Fresnel integral. These destructive interferences can reduce the beam intensity at the focus spot 32 to a value below the plasma threshold and thus preventing the laser beam 10 from photodisrupting the target region and from executing the surgical cuts along the surgical scan-pattern, instead leaving uncut regions behind. In some cases, the single focus spot may even break up into multiple foci, as shown later.

FIGS. 2A-B illustrate a related effect of corneal wrinkling. FIG. 2A illustrates that in the absence of corneal wrinkling the focus spot 32 of the laser beam 10 can have a near diffraction limited size of a few microns for a laser beam 10 with wavelength in the 500-1,500 nm range. The scanning delivery system and optics can be designed to deliver the laser beam 10 with an intensity to this focus spot 32 that marginally exceeds the plasma or photodisruption threshold everywhere in the surgical volume and thus is capable of executing the surgical cuts without leaving uncut regions behind.

FIG. 2B illustrates that when the vacuum suction or pressure of the PI 20 creates wrinkles 7 in the cornea 2, then the wrinkles 7 can redirect and refract some beam components to go through the plane of the focus spot 32, or focal plane, of the unwrinkled case smeared over an enlarged aberration focus spot 32. The increase of the focus spot area decreases the beam intensity, possibly below the plasma threshold. Besides causing destructive interference of the phase factors of the beam components, this focus-spot-smearing is an additional mechanism by which corneal wrinkling can reduce the beam intensity below the plasma threshold.

Finally, FIG. 2C illustrates a specific case of the problem in FIG. 2B: the formation of a single localized defect or wrinkle 7, created by the vacuum suction or the pressure of the PI 20. As before, the localized defect or wrinkle 7 can redirect or refract the laser beam 10 so that when the laser beam 10 goes through the focal plane, its beam components are smeared out over the enlarged aberration focus spot 32. As before, the increase of the focus spot area decreases the beam intensity, possibly reducing it below the plasma threshold.

FIGS. 3A-C illustrate one more negative effect of corneal wrinkling. FIG. 3A illustrates the previously discussed redirection of beam components in more detail. Three beam components are tracked explicitly. Visibly, the $1^{st}$, $2^{nd}$ and $3^{rd}$ beam components are redirected and refracted differently by the wrinkle 7. The $1^{st}$ and $3^{rd}$ beam components fall on the two sides of the wrinkle 7 that are relatively straight. Therefore, while the $1^{st}$ or $3^{rd}$ beam components get redirected, their focus spots do not get enlarged substantially and thus their beam intensity does not get reduced substantially. In contrast, the $2^{nd}$ beam component is propagating through the substantially curved wrinkle center 41 and thus gets refracted into a wider spatial angle, having its beam smeared out to an enlarged focus spot 32 and therefore having its beam intensity substantially reduced.

FIG. 3B illustrates that the location of the focus spot 32 of the entire laser beam 10 relative to the wrinkle center 41 controls which beam components are present in a laser beam 10 delivered to a particular direction.

FIG. 3B, top panel illustrates the focus spot 32 being in a left focus spot position, left of the wrinkle center 41. In this case the laser beam 10 includes only the $1^{st}$ and $2^{nd}$ beam components, resulting in a beam intensity profile that has one peak from the $1^{st}$ beam component with an intensity above the plasma threshold and a broad feature from the $2^{nd}$ beam component, smeared out to such a degree that its beam intensity is reduced below the plasma threshold. Therefore, the overall beam intensity profile exhibits a narrow peak, noticeably shifted to the left from the center of the focus spot 32. Thus, the laser beam 10 in the left focus spot position cuts the target tissue only partially, only at the location of the peak of the $1^{st}$ beam component but not at the location of the smeared $2^{nd}$ beam component. Moreover, the resulting partial cut will even be shifted from its intended location.

FIG. 3B, center panel illustrates that analogously, when the focus spot 32 is in the central focus spot position around the wrinkle center 41, the laser beam 10 includes all three beam components. In this central focus spot position the sides of the wrinkle 7 redirect the 1 and $3^{rd}$ beam components to separate side peaks, while the wrinkle center 41 again smears out the $2^{nd}$ beam component, reducing its intensity. This results in the shown two peaks in the beam intensity profile.

FIG. 3B, bottom panel illustrates the case when the focus spot 32 is in the right focus spot position, to the right of the wrinkle center 41. In this case the laser beam includes only the $2^{nd}$ and $3^{rd}$ beam components, resulting in one peak in the beam intensity profile, noticeably shifted to the right from the center of the focus spot 32.

As mentioned above, the laser systems are often designed so that the beam intensity exceeds the plasma threshold only marginally. Therefore, in the above three cases the beam intensity profile may remain above the plasma threshold only at the peaks of the $1^{st}$ and $3^{rd}$ beam components, whereas it may dip below the plasma threshold for the $2^{nd}$ beam component, smeared out by the wrinkle center 41. Correspondingly, in the left focus spot position the laser beam 10 may create a cut shifted to the left from the center of the focus spot 32; in the central focus spot position the laser beam 10 may create two cuts, shifted to the left and to the right from the center, and finally in the right focus spot position the laser beam 10 may create a cut shifted to the right from the center of the focus spot 32. Further, as mentioned before, these cuts can be only partial cuts, limited to portions of the beam cross section.

FIG. 3C illustrates how a linear scan-pattern 42 can get distorted in the presence of a wrinkled cornea. Such a linear scan-pattern 42 is typical for a capsulotomy (over a short segment, eventually looping around in a circle). In a typical case the laser beam 10 is scanned along a scanning direction 44 that is not parallel with a valley of the wrinkle center 46. When the focus spot 32 of the laser beam 10 is scanned left of the wrinkle center 46 through a left focus spot position, the laser beam 10 can create a distorted cut 48 instead of the planned linear scan-pattern 42, shifted to the left from the intended linear scan-pattern 42 as in the top panel of FIG. 3B. When the focus spot 32 is scanned through the central focus spot position, the distorted cut 48 can contain two off-center cuts, shifted to the left and to the right from the single cut of the linear scan-pattern 42, as in the center panel of FIG. 3B. Finally, when the focus spot 32 is scanned through the right focus spot position, the laser beam 10 can create a single cut again, only this time shifted to the right from the linear scan-pattern 42, as in the bottom panel of FIG. 3B.

FIG. 3C illustrates the resulting overall distorted cut 48: instead of the intended linear cut of the linear scan-pattern 42 that would have been created in the absence of the corneal wrinkle 7, a jagged, staggered, partially double-valued cut gets created when the laser beam 10 is scanned across a wrinkled cornea.

FIGS. 4A-B illustrate the analogous problem for a two dimensional (2D) scan-pattern 50. Such a 21) scan-pattern 50 can be used when an ophthalmic layer is to be cut, or a volume is to be photodisrupted. The laser beam 10 can be scanned along the 2D scan-pattern to create a densely packed layer of photodisrupted bubbles. This photodisrupted layer can effectively cut apart the tissue segments on its two sides. However, if the laser beam 10 is distorted by a wrinkled cornea, at several of the intended spots of the scan-pattern 50 the beam intensity may be reduced below the plasma threshold, and thus the laser beam 10 may fail to create the photodisrupted bubbles, as shown in FIG. 4A.

FIG. 4B illustrates that the beam intensity may be reduced below the plasma threshold for extended "no-cut regions" or "uncut regions" of the size d along a typical scan line 52, where d can be comparable to the size of the corneal wrinkles 7. In typical ophthalmic cases, d can vary from about 10 microns to beyond 1 millimeter. Referring back to FIG. 4A, these uncut regions can have a spatial extent beyond a millimeter in one, two or even all three dimensions. Therefore, when the scanning of the laser beam 10 is finished, the intended surgical cuts will be interrupted by extended no-cut regions.

The surgeon may attempt to cut these no-cut regions by re-scanning the entire scan pattern or portions of the scan-pattern 50. However, this is not very effective, since the same wrinkles are still present in the cornea, giving rise to the same aberrations. Thus, the same regions will remain uncut during the second scan. Re-scanning is also time-consuming. Every time the surgeon is forced to repeat a surgical step, valuable surgical time is spent, increasing the probability of undesirable outcomes.

Therefore, the surgeon may be forced to cut the uncut regions manually to complete the surgery, possibly creating jagged edges, leading to the formation of tears in the ophthalmic tissue. These undesirable effects call out for improvements in the surgical laser systems that reduce or eliminate the formation of the uncut regions.

Briefly and generally, embodiments of the invention offer solutions to the above problems by providing a surgical laser system that includes a laser engine, configured to generate a laser beam of laser pulses; a scanning delivery system, configured to direct the laser beam to a target region, and to scan the laser beam along a scan-pattern in the target region; and an adjustable pupil system, configured to modulate the laser beam.

Other embodiments include a method of adjusting a pupil of a laser beam, the method including: generating a laser beam of laser pulses with a laser engine; directing the laser beam to a target region with a scanning delivery system; scanning the laser beam along a scan-pattern in the target region with the scanning delivery system; and performing a modulation of the laser beam with an adjustable pupil system.

BRIEF DESCRIPTION OF THE DRAWINGS

FIGS. 1A-E illustrate an effect of a wrinkled cornea on an ophthalmic surgical laser beam.

FIGS. 2A-C illustrate an enlargement of a focus spot because of corneal wrinkling.

FIGS. 3A-C illustrate an effect of corneal wrinkling on a linear cut.

FIGS. 6A-C illustrate an effect of the adjustable pupil system on a beam intensity in the context of a one dimensional scan-pattern.

FIGS. 7A-B illustrate an effect of the adjustable pupil system on a beam intensity in the context of a two dimensional scan-pattern.

FIGS. 13A-F illustrate hard pupil embodiments of an adjustable pupil system.

DETAILED DESCRIPTION

To address the above described problem of the appearance of extensive no-cut regions caused by the corneal wrinkles distorting the laser beam, this patent document describes embodiments of a surgical laser system that includes embodiments of a spatio-temporal beam modulator, in particular an adjustable pupil system.

Figure 5:
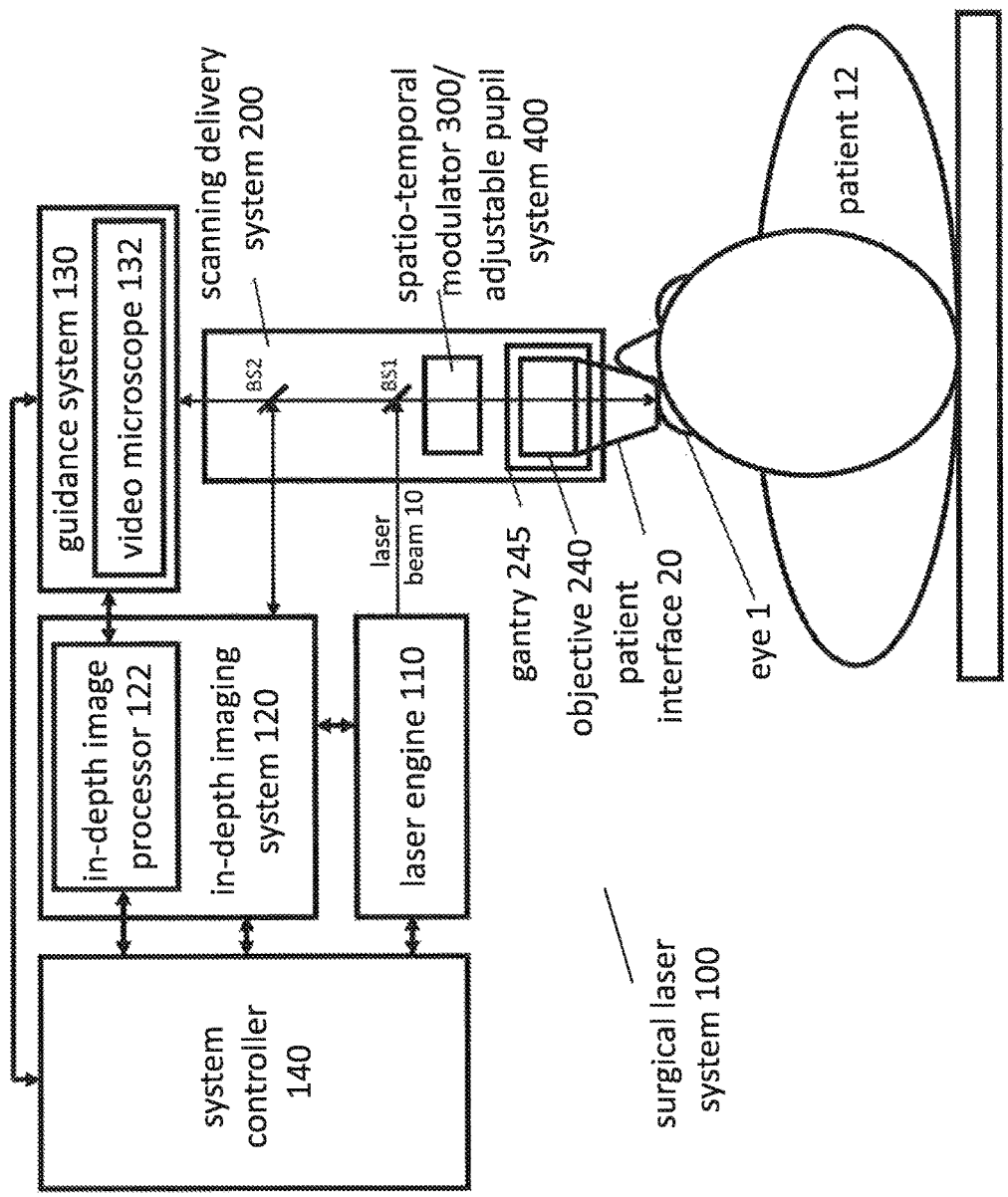
FIG. 5 illustrates an ophthalmic surgical laser system with an adjustable pupil system.

FIG. 5 illustrates an ophthalmic surgical laser system 100 that can include such a spatio-temporal beam modulator or adjustable pupil system. The ophthalmic surgical laser system 100 can include a laser engine 110 that can generate a pulsed laser beam 10 to be directed and scanned into the eye 1. The laser system 100 can also include an in-depth imaging system 120 to generate images of the internal structure of the eye 1. The in-depth imaging system 120 can provide one or more in-depth images for the ophthalmic surgeon to increase the precision of the ophthalmic procedure. The in-depth imaging system 120 can be configured to generate a stereoscopic microscope image, a video-image, a Scheimpflug image, or an Optical Coherence Tomographic (OCT) image. The image can be analyzed by an image processor 122 of the in-depth imaging system 120.

The laser system 100 can also include a guidance system 130 to provide guidance information for the ophthalmic surgeon. In some embodiments, the guidance system 130 can include a video microscope 132 to display a video image of the eye 1. In others, the guidance system 130 can also include an in-depth display to display the in-depth image created by the in-depth imaging system 120. In yet others, the guidance system 130 can display both the video image and the in-depth image.

In some embodiments, the guidance system 130 can include a guidance display to guide the surgeon based on the result of the processing of the in-depth image of the imaging system 120 by the image processor 122. In others, the guidance system 130 can display the results of a processing of the video image of the video microscope 132 by a video image processor. For example, the guidance display of the guidance system 130 can include a target pattern or a crosshair pattern overlaid on the video image of the eye 1 to indicate a position of an optical center or axis of the laser system 100, thus allowing the surgeon to determine the position of the eye 1 relative to the optical axis. In other embodiments, the guidance system 130 can display a reference of the laser system 100 overlaid on the in-depth image, generated by the in-depth imaging system 120. These guidance displays can be used by the surgeon to dock the laser system 100 onto the eye with high precision and to plan and control the ophthalmic surgical procedure. The operations of the laser system 100 can be controlled and coordinated by a system controller 140.

The pulsed laser beam 10, generated by the laser engine 110 can be coupled into a scanning delivery system 200 at a beam splitter BS1. The laser engine 110 can be capable of generating the pulsed laser beam 10 with a pulse length in the femtosecond range (1-1,000 fs) or in the picosecond range (1-1,000 ps). The scanning delivery system 200 can redirect and deliver the pulsed laser beam 10 into the eye 1 of a patient 12 through an objective 240. The objective 240 can be movable by a gantry 245. The patient interface PI 20 can be attachable to the objective 240 to immobilize the targeted eye 1 relative to the objective 240 and to provide a controlled entry for the laser beam 10 into the eye 1.

Finally, the scanning delivery system 200 can include a spatio-temporal modulator (STM) 300, or space-time modulator 300, configured to perform a space- and time dependent modulation of the laser beam 10. The spatio-temporal modulator 300 can create a modulated component $\Phi_{mod}$ for the aberration function $\Phi$ in the Huygens-Fresnel integral that is additive to $\Phi_{ab}$, the aberration caused by the wrinkled tissue and possibly the surgical laser system: $\Phi = \Phi_{ab} + \Phi_{mod}$.

Classes of embodiments of the spatio-temporal modulator 300 can perform their function while keeping a pupil of the laser system 100 unchanged. Other implementations, like an adjustable pupil system APS 400, belong to that class of embodiments of the spatio-temporal modulator 300 that can modify or adjust a pupil of the beam as part of their operation.

FIGS. 6-9 illustrate the general principles of operation that are relevant for all embodiments of the spatio-temporal modulator 300, including embodiments of the adjustable pupil system 400. Sometimes these embodiments will be summarily referred to as SIM 300/APS 400. FIGS. 10-14 illustrate particular embodiments of the adjustable pupil system 400.

Before proceeding with the detailed description, it is pointed out here that some existing systems attempt to reduce the effects of beam distortion by performing a diagnostics of the beam to determine the beam distortion by using e.g. a wavefront analyzer and then modifying the beam based on a feedback, generated from the determined beam distortion. These beam-diagnostic feedback systems increase the complexity of the system considerably, also increasing the number of elements that can (i) break down and require servicing, and (ii) slow down the system's response time and operating speed.

In contrast, some embodiments of the STM 300/APS 400 are operable without a beam diagnostic system or a wavefront analyzer as part of a feedback system.

Instead of utilizing such diagnostic feedback systems, in some embodiments the STM 300/APS 400 can be configured to randomize the phase or the amplitude of the beam components of the laser beam on a modulation length and a modulation time. Such a randomization of the phases or amplitudes can be a comparably effective way to reduce the beam distortions caused by corneal wrinkling, while it does not add to the complexity of the laser system 100 and so it does not slow down its performance, require additional servicing, or increase the overall costs.

Figure 1C:
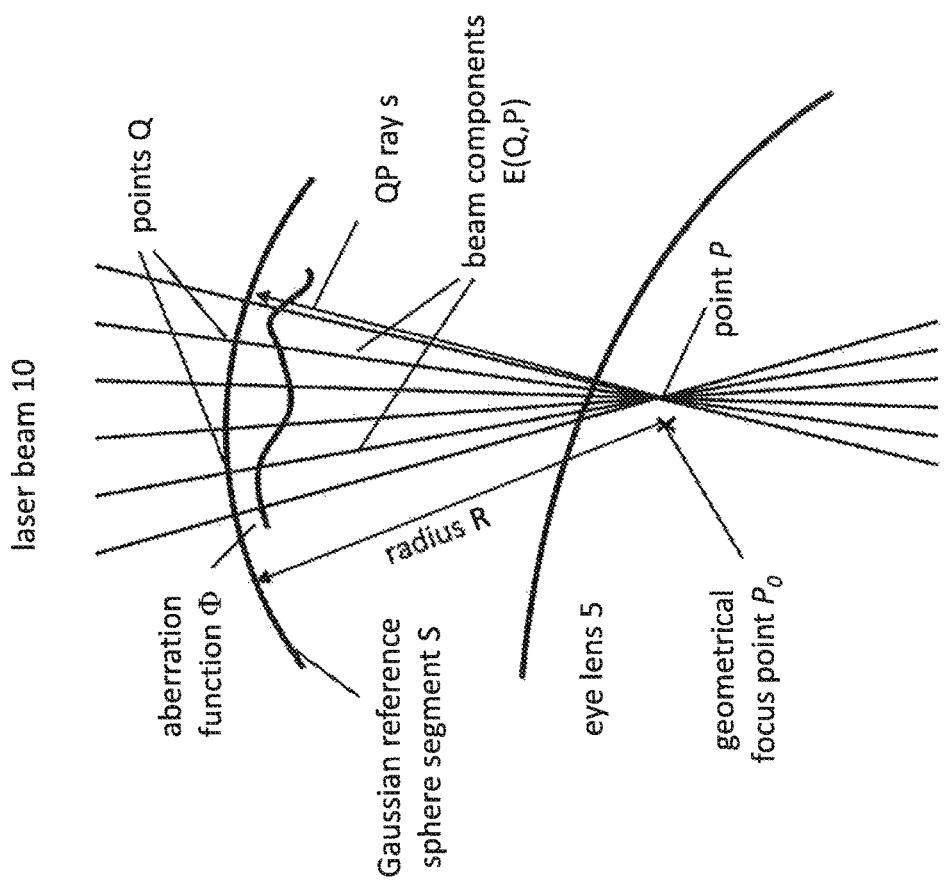
Figure 1E:
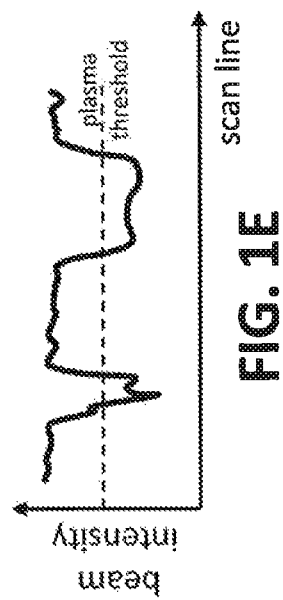
Figure 1D:
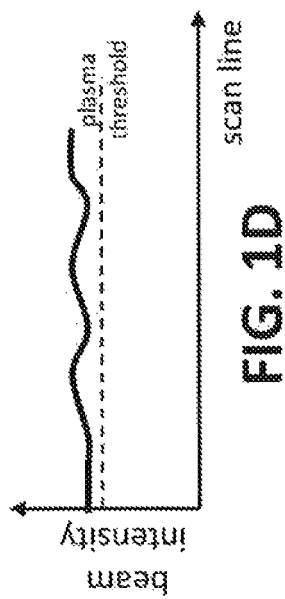
Figure 2C:
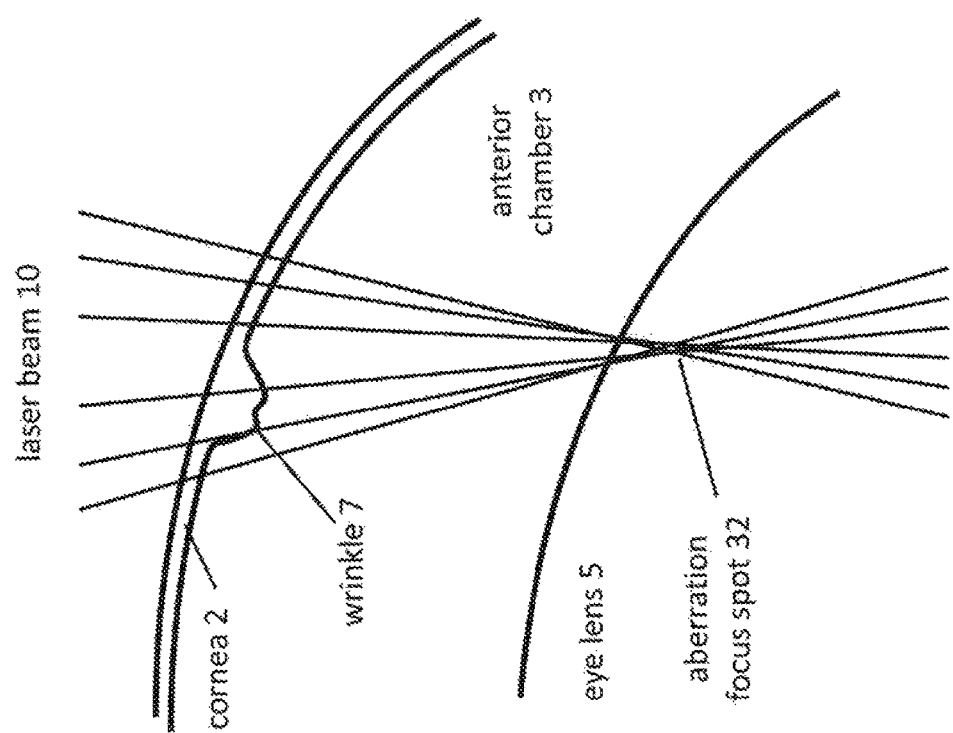
Figure 4A:
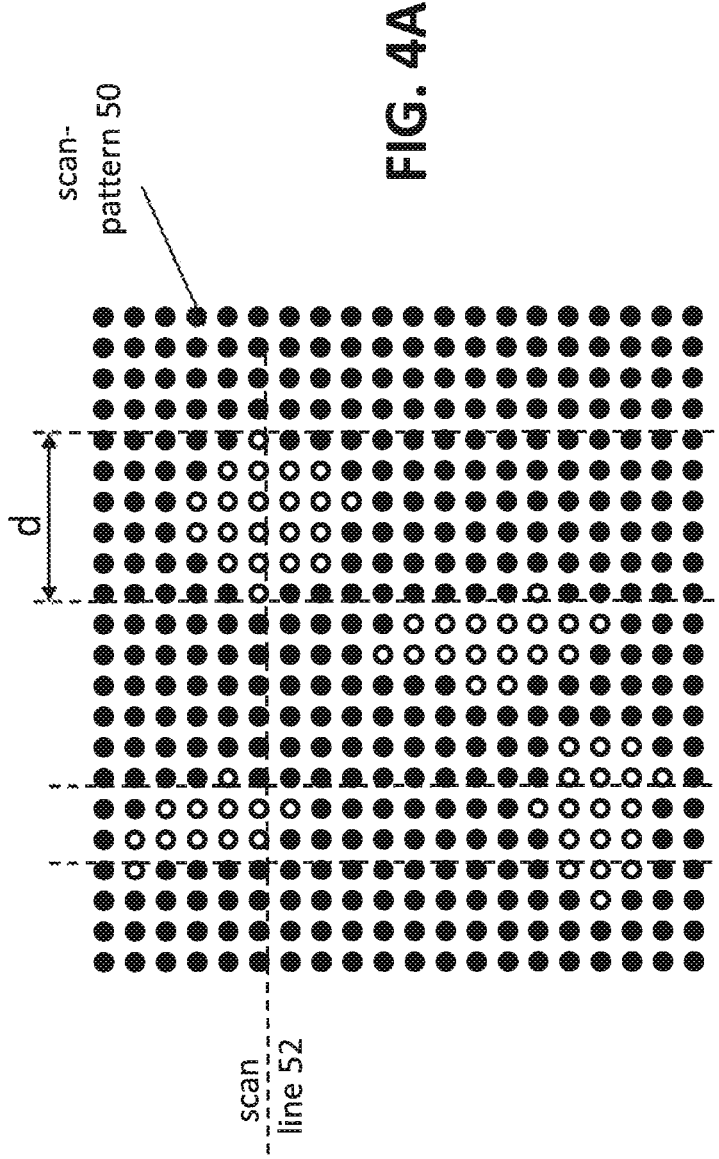
FIGS. 4A-B illustrate an effect of corneal wrinkling on a two dimensional cut.
Figure 4B:
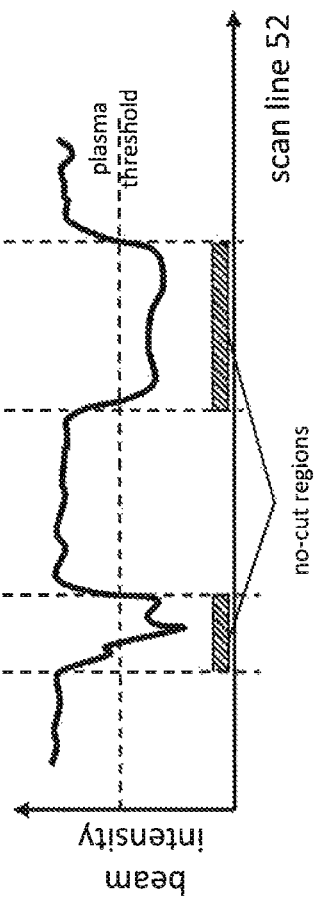

FIGS. 6A-C illustrate the operation of the STM 300/APS 400 in more detail. FIG. 6A illustrates the beam intensity with the STM 300/APS 400 fixed at t, i.e. what the beam intensity would be, should the focus spot 32 of the laser beam 10 be scanned along a scan line while keeping the STM 300/APS 400 fixed in its configuration of time t. As it has been pointed out already in relation to FIG. 4B, corneal wrinkles 7 can reduce the beam intensity below the plasma threshold in extended no-cut or uncut regions, whose size can approach or exceed a millimeter. In the example of FIG. 6A, at the time t the focus spot 32 is scanned through a point x that belongs to such a no-cut region with the STM/APS in its configuration at t where the corneal wrinkling caused such a destructive interference that the beam intensity is reduced below the plasma threshold over an extended no-cut region.

Should the STM 300/APS 400 remain fixed in its configuration of time t while the scanning of the focus spot continues, the focus spot will continue to scan through a region where the intensity of the laser beam is reduced by the corneal wrinkles below the plasma threshold over an extended no-cut region.

FIG. 6B illustrates that the STM 300/APS 400 can change its configuration in a modulation time $\Delta t$ and shows what the beam intensity would be if the STM 300/APS 400 were fixed in its new configuration at the time $t+\Delta t$ and the laser beam 10 scanned along the same scan line. Visibly, the STM 300/APS 400 can change the spatial modulation of the phase factors of the propagating electric fields in the modulation time $\Delta t$ after the time t so that the no-cut regions of time t get either shifted by an amount comparable to their size (right no-cut region of FIG. 6A shifted in FIG. 6B), or get modified, reduced, or even eliminated altogether (left no-cut region of FIG. 6A having disappeared in FIG. 6B). In this same modulation time $\Delta t$, the scanning of the focus spot 32 may progress from x to $x+\Delta x$. As shown in FIG. 6B, the STM 300/APS 400 can be configured to spatio-temporally modify the beam so that its no-cut regions get shifted or modified to such a degree that at the time $t+\Delta t$ the location $x+\Delta x$ of the focus spot 32 falls outside the modified no-cut regions.

FIG. 6C summarizes the beam modification caused by the above-described operation of the STM 300/APS 400. To substantially reduce the spatial extent of the no-cut regions, the STM 300/APS 400 can be configured to rapidly change the spatial modulation of the laser beam 10. This space and time dependent, or "spatio-temporal" modulation of the laser beam 10 can cause the laser beam 10 to exhibit an effective beam intensity instead of the "fixed STM" beam intensities of FIGS. 6A-B as the focus spot 32 is scanned along the scan line.

In particular, even if the beam components exhibit a destructive interference at a time t at a position x, forcing the beam intensity below the plasma threshold and thus the focus spot 32 into a no-cut region, the STM 300/APS 400 can cause the beam components to change their destructively interfering phase factors in a short modulation time $\Delta t$, thus shifting, modifying or eliminating the no-cut region at the location $x+\Delta x$ by the time $t+\Delta t$ the laser beam 10 is scanned through the location $x+\Delta x$ along the scan line. Thus, the operation of the STM 300/APS 400 can make the scanned laser beam 10 to exhibit an effective beam intensity where the spatial extent of the "fixed STM/APS" no-cut regions is reduced to much shorter effective no-cut regions. Therefore, the spatio-temporal modulation of the beam components by the STM 300/APS 400 can cause the laser beam 10 to maintain its beam intensity above the plasma threshold over a much higher fraction of the scan-pattern and to photodisrupt the target tissue successfully throughout the scan-pattern, interrupted only by much-shortened no-cut regions.

In some embodiments, the STM 300/APS 400 can be configured to reduce a length of a no-cut region, or equivalently an un-photo-disrupted scan-segment by a factor of more than 2 compared to the length of an un-photo-disrupted scan-segment made by the same surgical laser system 100 at the same location with the same corneal wrinkling but without the STM 300/APS 400.

FIGS. 7A-B illustrate the analogous reduction of the length or spatial extent of the no-cut regions when the laser system 100 that includes an STM 300/APS 400 follows a 21) scan-pattern 50. FIG. 7B illustrates that when the laser system follows the 2D scan-pattern 50, the operation of the STM 300/APS 400 can give rise to an effective beam intensity with no-cut regions whose size has been substantially reduced in both dimensions to the size of essentially a single bubble, as clear from a comparison of FIGS. 4A-B to FIGS. 7A-B.

Figure 8B:
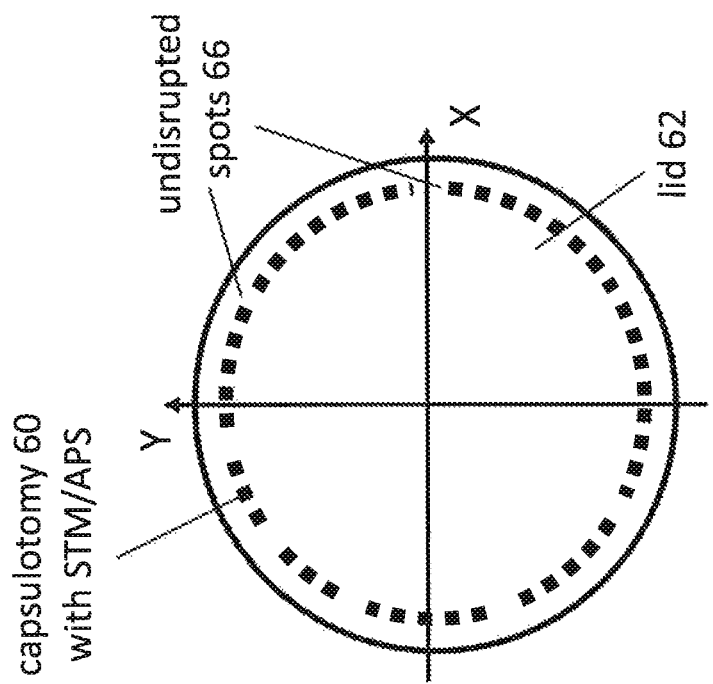
FIGS. 8A-B illustrate an effect of the adjustable pupil system on a photodisruption efficiency of a capsulotomy.
Figure 8A:
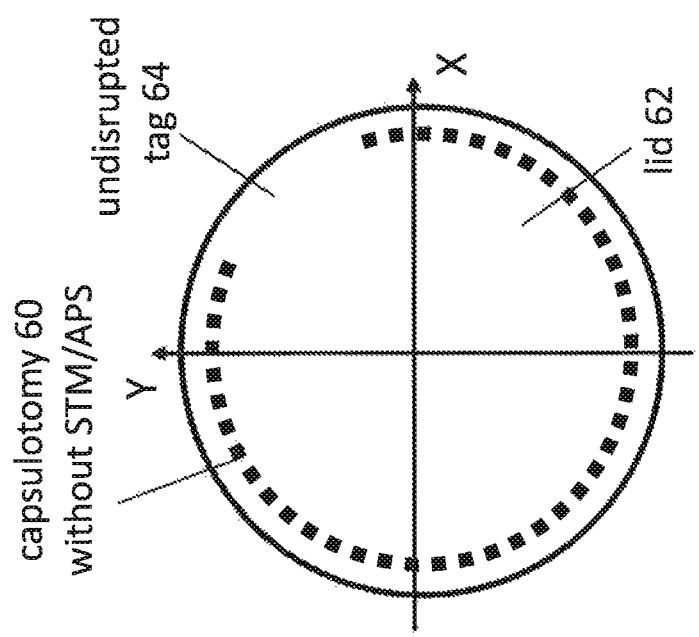

FIGS. 8A-B illustrate the operation of the STM 300/APS 400 in the context of a capsulotomy 60. FIG. 8A shows a typical circular capsulotomy 60, a circular or elliptical cut of the capsular bag, creating a lid 62. Having performed the capsulotomy 60, the surgeon removes the lid 62 to extract the lens 5 after the lens photodisruption.

However, in existing laser systems a conical wrinkle 7 can reduce the intensity of the surgical laser beam 10 below the plasma threshold over a substantial no-cut region, forming an undisrupted tag 64. This undisrupted tag 64 requires the surgeon to manually complete the capsulotomy 60, possibly tearing the capsular bag or creating a jagged capsulotomy when removing the circular lid 62. Either of these possibilities can substantially reduce the precision of the cataract procedure itself and the subsequent insertion of an Intra Ocular Lens, or IOL, into the capsular bag.

FIG. 8B illustrates a capsulotomy 60, created by a laser system 100 that includes the STM 300/APS 400. As described above, in the presence of the conical wrinkles 7 the STM 300/APS 400 can modulate the beam components to substantially shorten the length of the no-cut regions 64 into undisrupted spots 66. During cataract surgeries with such laser systems, when the surgeon removes the lid 62, the tearing of the capsular bag at the short and localized undisrupted spots 66 will be minimal and well-controlled, thus maintaining the high precision attainable in the absence of conical wrinkles.

Figure 9A:
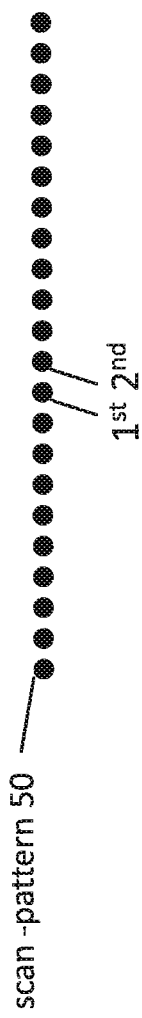
FIGS. 9A-C illustrate a location of a first and second spot along a scan line, along a returning scan-line and along a returning scan-segment.

FIG. 9A illustrates that in some surgical laser systems 100 the STM 300/APS 400 can be configured to perform the space- and time dependent modulation of the laser beam components within a modulation time Δt less than 10 times T, a repetition time of the laser pulses: T=1/f, f being the pulse repetition rate. In such embodiments, the modulation time Δt it takes for the STM 300/APS 400 to perform the spatio-temporal modulation, can be less than or comparable to the time T it takes the laser beam 10 to scan the focus spot 32 from a $1^{st}$ spot to a $2^{nd}$ spot, neighboring the $1^{st}$ spot or being very close to it.

In such embodiments the STM 300/APS 400 can shift or modify a potential no-cut region substantially while the focus spot 32 is scanned from the $1^{st}$ spot to the $2^{nd}$ nearby spot. Therefore, such an embodiment can reduce a potentially extended no-cut region to one or two un-photodisrupted spots, drastically improving the precision of the surgical procedure, performed by the laser system 100.

Figure 9B:
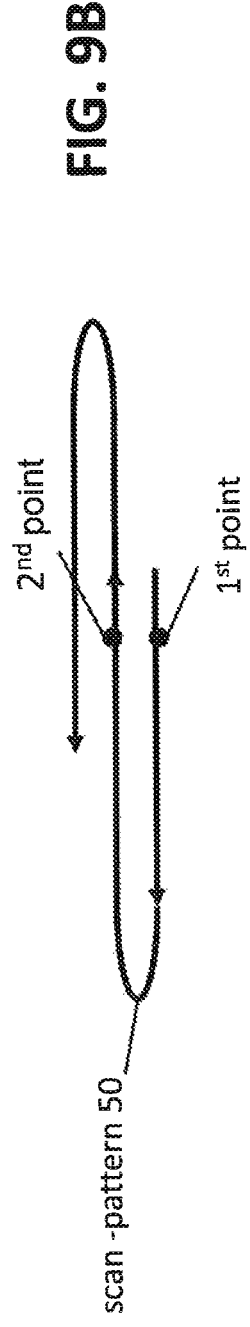

FIG. 9B illustrates that in some laser systems 100 the STM 300/APS 400 can be configured to perform the space- and time dependent modulation of the beam components within a modulation time Δt that is smaller than or equal to a return time T(return) of the scan-pattern 50. Here, the scan-pattern 50 can include a set of closely spaced lines connected by switchbacks or hairpin turns, for example to perform a 21) cut or layer cut. The return time T(return) can be a time the scanning of the laser beam 10 takes between passing a $1^{st}$ point on a first line of the scan-pattern 50 and passing a $2^{nd}$ point on a second line of the scan-pattern 50 nearest to the $1^{st}$ point, as shown.

In such embodiments, even if the beam intensity at the $1^{st}$ point is below the plasma threshold, by the time the scanning of the laser beam reaches the $2^{nd}$ point, the STM 300/APS 400 changed the beam modulation to such a degree that the effective beam intensity is likely to be restored to its above-the-plasma-threshold level. Therefore, such embodiments can reduce the transverse spatial extent of potential no-cut regions to that of the transverse line separation. As FIG. 48 illustrated, without the STM 300/APS 400 the corneal wrinkles 7 can form large no-cut regions with spatial extent in both the direction parallel and in the direction perpendicular or transverse to the direction of scanning. The embodiment of FIG. 9B can reduce this latter transverse extent of the no-cut regions substantially.

Figure 9C:
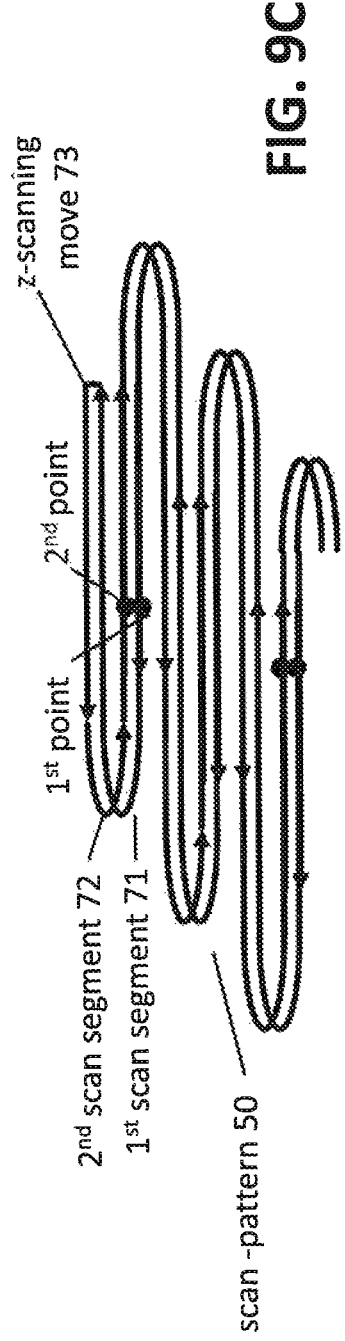

FIG. 9C illustrates that in some surgical laser systems 100 the STM 300/APS 400 can be configured to perform the space- and time dependent modulation of the beam components within a modulation time Δt less than a return time T(return) of the scan-pattern 50, wherein the scan-pattern 50 can include a set of closely spaced scan segments, and the return time T(return) can be a time the scanning of the laser beam 10 takes between passing a $1^{st}$ point on a $1^{st}$ scan-segment 71 of the scan-pattern 50 and a $2^{nd}$ point on a $2^{nd}$ scan-segment 72 of the scan-pattern 50, nearest to the first point. In the example of FIG. 9C, the first scan segment 71 can involve a first set of closely spaced lines in a transverse (x,y) plane, as in FIG. 9B. This can be followed by a z-scanning move 73 to a slightly anterior z coordinate along the optical axis of the laser system 100, connecting to the second scan segment 72 that includes a second set of closely spaced lines in the transverse (x,y) plane retracing the first scan segment 71 at the new slightly anterior z coordinate. Such cuts can be used to photodisrupt a volume of ophthalmic tissue, as is needed for the photodisruption of the lens 5 in the course of cataract surgery.

In sum, the list of the advantages of using the STM 300/APS 400 in the laser system 100 includes the followings. (i) When corneal wrinkles cause the appearance of uncut regions, a normal response with a typical laser system is to increase the energy of the laser beam so that no uncut region is left behind. However, such an increase of the beam energy can cause collateral damage in the form of overheating and shockwaves in the ophthalmic tissue. In laser systems that include the STM 300/APS 400, even in the presence of corneal wrinkling the surgical goals such as a clean capsulotomy can still be achieved without increasing the beam energy. This is so because, while the corneal wrinkles can still distort the laser beam to leave uncut regions, the inclusion of the STM 300/APS 400 substantially reduces the spatial extent of these uncut regions, and these short uncut regions can be comfortably cut manually later by the surgeon without causing jagged edges or tearing. Thus, laser systems with the STM 300/APS 400 eliminate the need to increase the pulse energy of the laser beam in the presence of corneal wrinkling. This aspect also allows laser systems with the STM 300/APS 400 to reduce the overall exposure time of the targeted ophthalmic tissues.

(ii) Referring back to FIGS. 3A-C, the jagged, double cut and sometimes discontinuous cut lines that can appear during a capsulotomy in the presence of corneal wrinkling can be also eliminated by the inclusion of the STM 300/APS 400 in the laser system 100.

(iii) Finally, incorporating the STM 300/APS 400 into the laser system 100 can also make re-tracing a surgical cut or portions of it much more effective. In an example, after performing a surgical beam scan the surgeon may observe that the scan still left an undesirably long uncut section, and may decide to rescan the uncut section. In a laser system without the STM 300/APS 400, the rescanning does not promise an improvement, as the corneal wrinkles will once again cause a destructive interference between the beam components, thus preventing the cut even during the rescan. In contrast, in a laser system that includes the STM 300/APS 400, by the time the uncut section is rescanned, the STM 300/APS 400 changes the beam modulation and thus substantially reduces or eliminates the destructive interference for the rescan of the uncut section. In other words, since the phases of the beam components are modulated differently during the first scan and the rescan, the interferences which were destructive during the first scan and gave rise to uncut portions, change substantially during the rescan, so that the uncut regions of the first scan get filled in by the subsequent rescan. Rescanning can include scanning along the same scanning track or scanning in the vicinity of the previous cut, preferably within the plasma-tissue interaction length. When cutting with a femtosecond laser, this plasma-tissue interaction length is typically the diameter of the laser-induced cavitation bubbles in the tissue, often in the 1-20 micrometer range. In an example, a capsulotomy can include performing repeated circular cuts at a sequence of z depths moving in a posterior-to-anterior direction, the circular cuts being separated by a few micrometers and thus creating a macroscopic cut shaped like a cylinder. Re-scanning can be performed as an intervention by the surgeon, as an intervention by the control system, or be pre-programmed into the control system software without feedback.

After having described the operation and impact of the STM 300/APS 400, various specific embodiments of the adjustable pupil system APS 400 are described next. It is recalled here that an optical system can accept an incident light or laser beam at a specific location with a specific cross-section or diameter: this is the so-called entrance pupil. The optical system can transmit the accepted beam and output it at another location with another specific cross-section and diameter: this constitutes the exit pupil. The optical system can restrict the incident beam and transmit only a fraction of the beam. This restriction can be carried out at the entrance pupil, the exit pupil, or at an internal pupil.

In some embodiments, this restriction of the beam can be carried out by a hard pupil, such as an aperture or a reflective surface with a diameter smaller than the beam diameter. In other embodiments, the entire beam may be transmitted but constrained to a smaller cross section by careful control of the beam diameter and location of the beam by other means, such as beam expanders and a beam scanner, such as a suitably oriented mirror pair. The cross section to which the beam is constrained is referred to as a soft pupil. In the present application, the entrance, exit, internal, hard and soft pupils will be collectively referred to as a pupil. The adjustable pupil system 400 can include an adjustable pupil, its actuator and its controlling system with the corresponding control software and protocol.

Since the location and size of the pupil relative to the optical axis impacts the length of the optical path of the beam components, adjusting the pupil modulates the phases of the beam components in the Huygens-Fresnel integral. Therefore, if a beam is distorted by a defect or distortive target region, such as the wrinkles 7 in the cornea, adjusting the adjustable pupil system 400 can potentially introduce phase modulations that can compensate some of the distortions caused by the defect and thus reduce the aberrations of the laser beam. For all these reasons, a surgical laser system 100 that includes the adjustable pupil system 400 offers the functionality of compensating and reducing aberrations of the laser beam 10 caused by distortions in the target region.

Figure 10A:
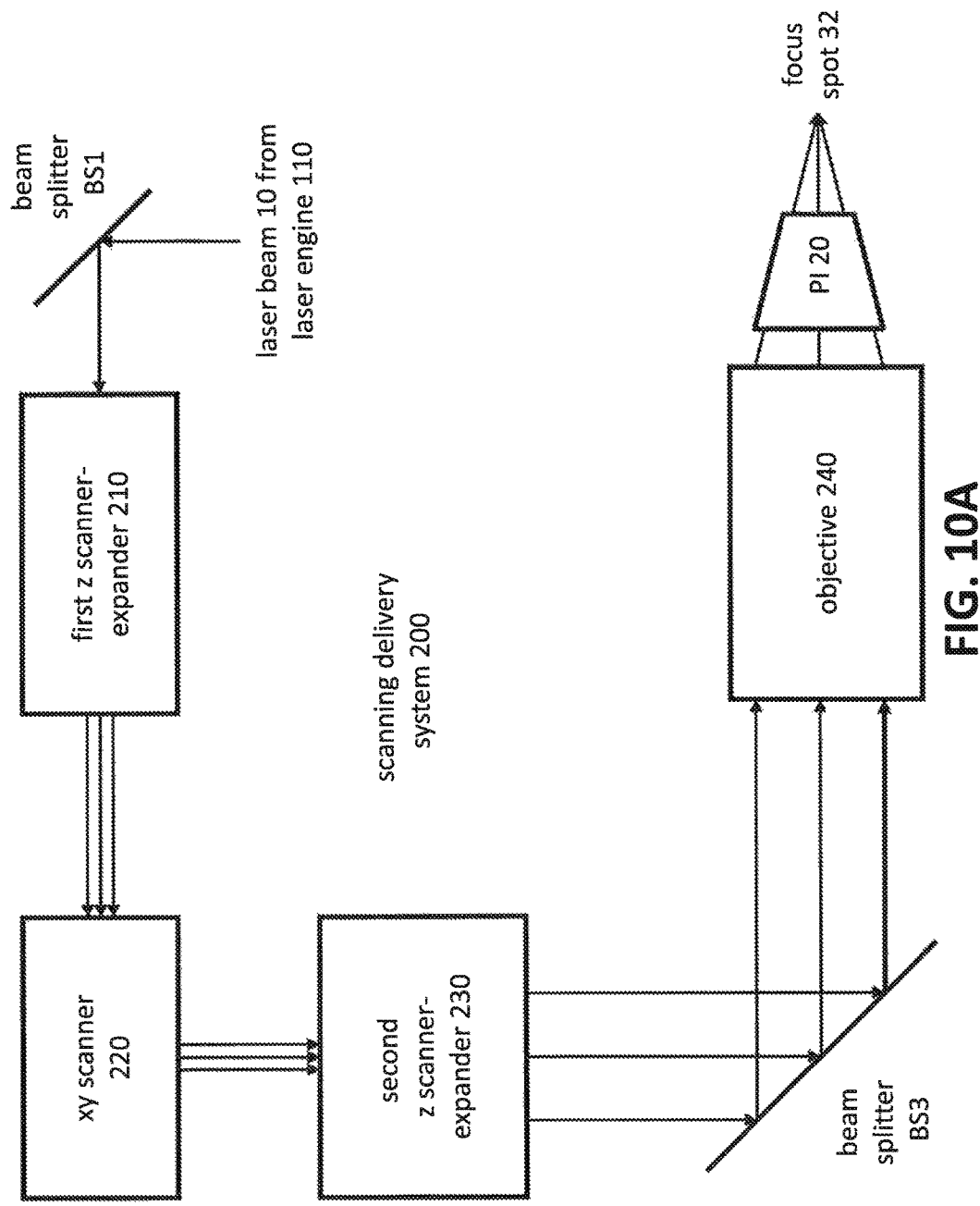
FIGS. 10A-B illustrate a scanning delivery system and possible locations of an adjustable pupil system in different embodiments.

FIG. 10A illustrates an embodiment of the scanning delivery system 200 in more detail. The laser beam 10 can enter the scanning delivery system 200 via the beam splitter BS1 and can proceed to a first z scanner-expander 210 that can expand a radius of the laser beam 10 and can also play a part in scanning the z longitudinal or depth coordinate of the focus spot 32 in the target region or tissue. From the first z scanner-expander 210, the expanded laser beam 10 can propagate to an xy scanner 220 that is configured to scan the focus spot 32 in the transverse (x,y) plane in the target region or tissue.

From the xy scanner 220, the laser beam 10 can propagate to a second z scanner-expander 230 whose functions can be similar to that of the first z scanner-expander 210. Various embodiments of the scanning delivery system 200 may include only one of the two z scanner-expanders 210 and 230. The functions of the z scanner-expanders 210 and 230 can include scanning the z longitudinal or depth coordinate of the focus spot 32 in the target region or tissue. The scanning delivery system 200 can also include the objective 240, to which the laser beam 10 may be redirected by a beam splitter BS3. The objective 240 can focus the expanded laser beam into a high numerical aperture (high NA) focused beam and deliver it to the target region through the patient interface (PI) 20. Generating a high NA beam can ensure that the laser beam 10 causes photodisruption only at the intended z depth or longitudinal coordinate, thus avoiding collateral damage posterior or anterior relative to the target region. In some embodiments, NA can be in the 0.15-0.45 range. In some others, it can be in the 0.25-0.35 range.

Figure 10B:
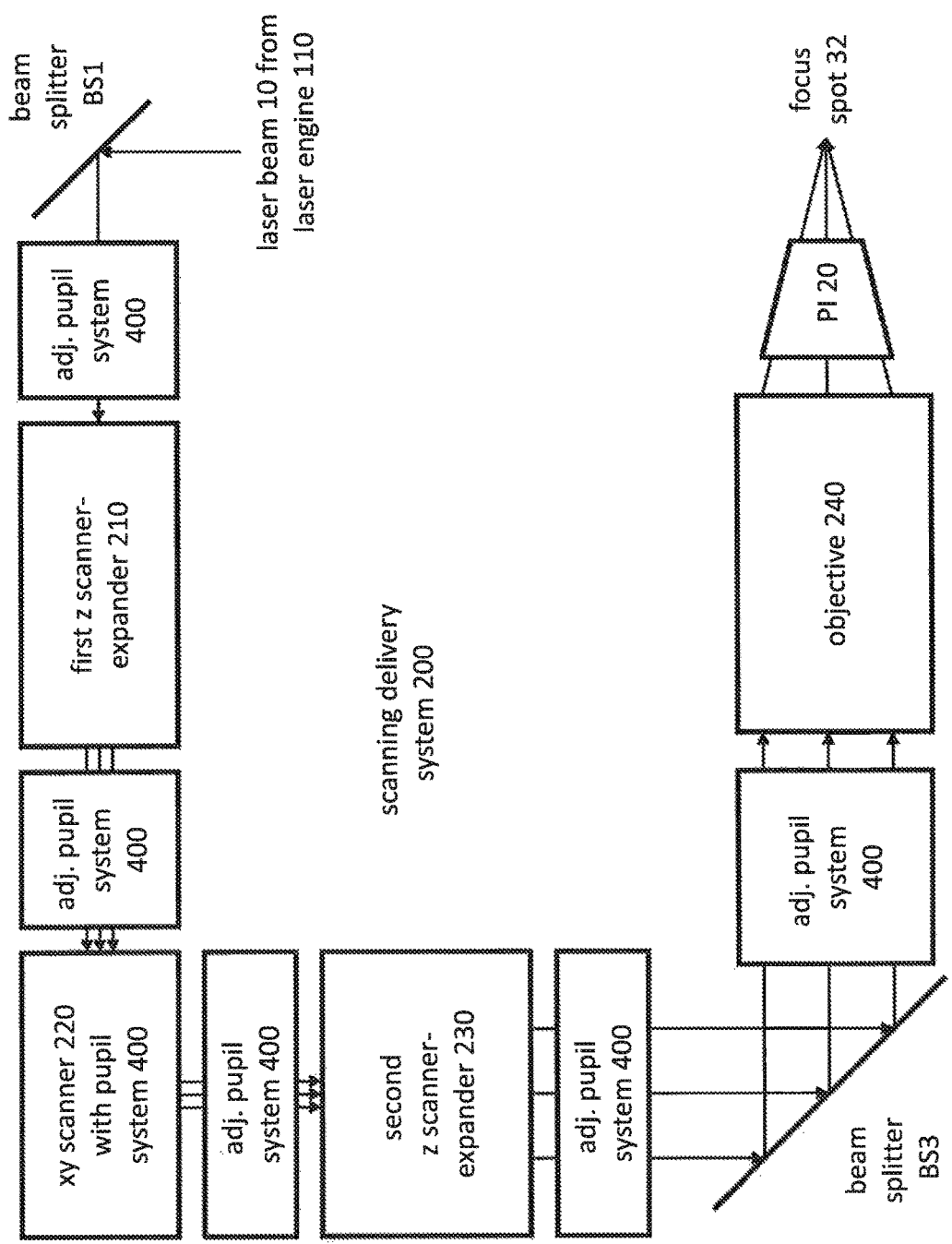

FIG. 10B illustrates that in various embodiments of the scanning delivery system 200 the APS 400 can be disposed at different locations along an optical path of the laser beam 10, including: before the first z scanner-expander 210, between the first z scanner-expander 210 and the xy scanner 220, integrated within the xy scanner 220, between the xy scanner 220 and the second z scanner-expander 230, and between the second z scanner 230 and the objective 240. The APS 400 can be disposed at any one of these locations.

With the above broad definition of a pupil, the various implementations of the APS 400 can include a transmissive, an absorptive or a reflective adjustable pupil system, inserted into the beam path accordingly. A transmissive pupil can include an aperture, a reflective pupil can include a surface with a limited-area reflective region, and an absorptive pupil can include a disc with a spatially dependent absorption coefficient.

Figure 11:
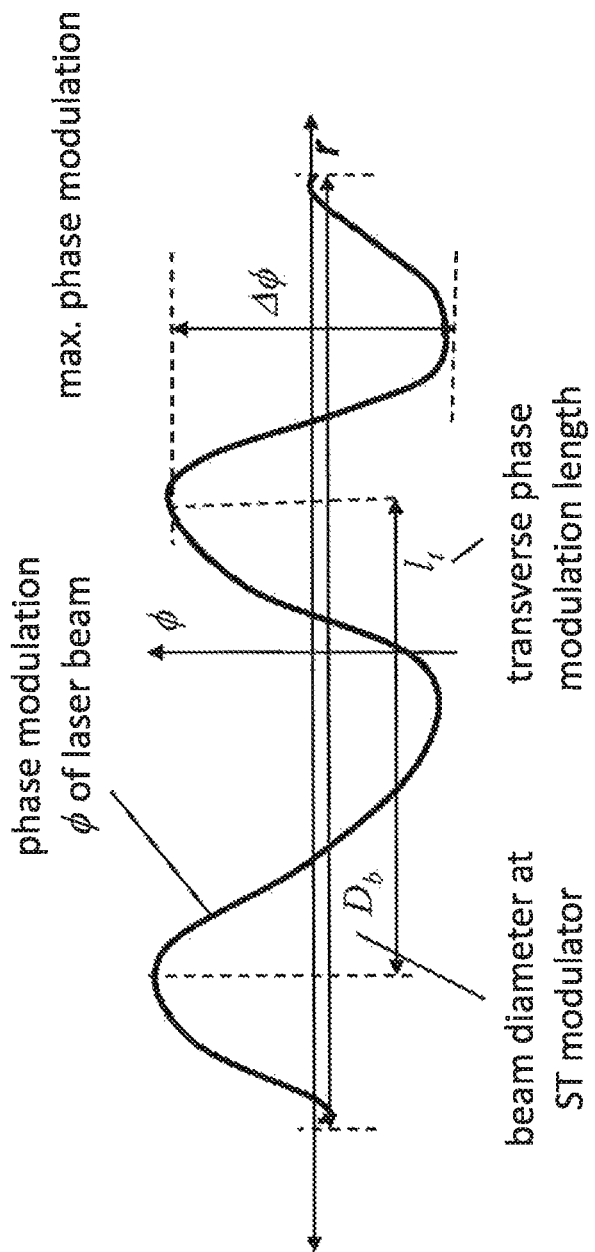
FIG. 11 illustrates a phase modulation by an adjustable pupil system.

FIG. 11 illustrates that the APS 400 can be configured to perform the space- and time dependent modulation of the laser beam by modulating the phase or aberration $\Phi$ of the beam components. FIG. 11 illustrates that the phase $\Phi$ can be modulated across the beam diameter $D_b$ at the APS 400 on a transverse phase modulation length $l_t$, where the transverse modulation length $l_t$ can be less than the beam diameter $D_b$ at the APS 400. When the modulation length $l_t$ is less than the beam diameter $D_b$, the APS 400 can modulate the phases of the beam components differently, reducing or eliminating the destructive interferences at the focal plane in the target region, caused by distortion centers, such as the corneal wrinkles 7. In some embodiments of the laser system 100, $D_b$ can be in the range 5-30 mm, in others, in the range of 10-20 mm. $l_t$ can be in the range of 0.1-5 mm, in some cases in the 0.2-1 mm range. Finally, in some embodiments, $\Delta\phi$, the maximum of the phase modulation can be at least $\pi/4$.

FIGS. 12-14 illustrate various embodiments of the APS 400. These embodiments can be used effectively to modulate the phase factors $\Phi$ of the beam components of the laser beam 10 by adjusting a pupil of the laser system 100.

Figures 12A, 12B:
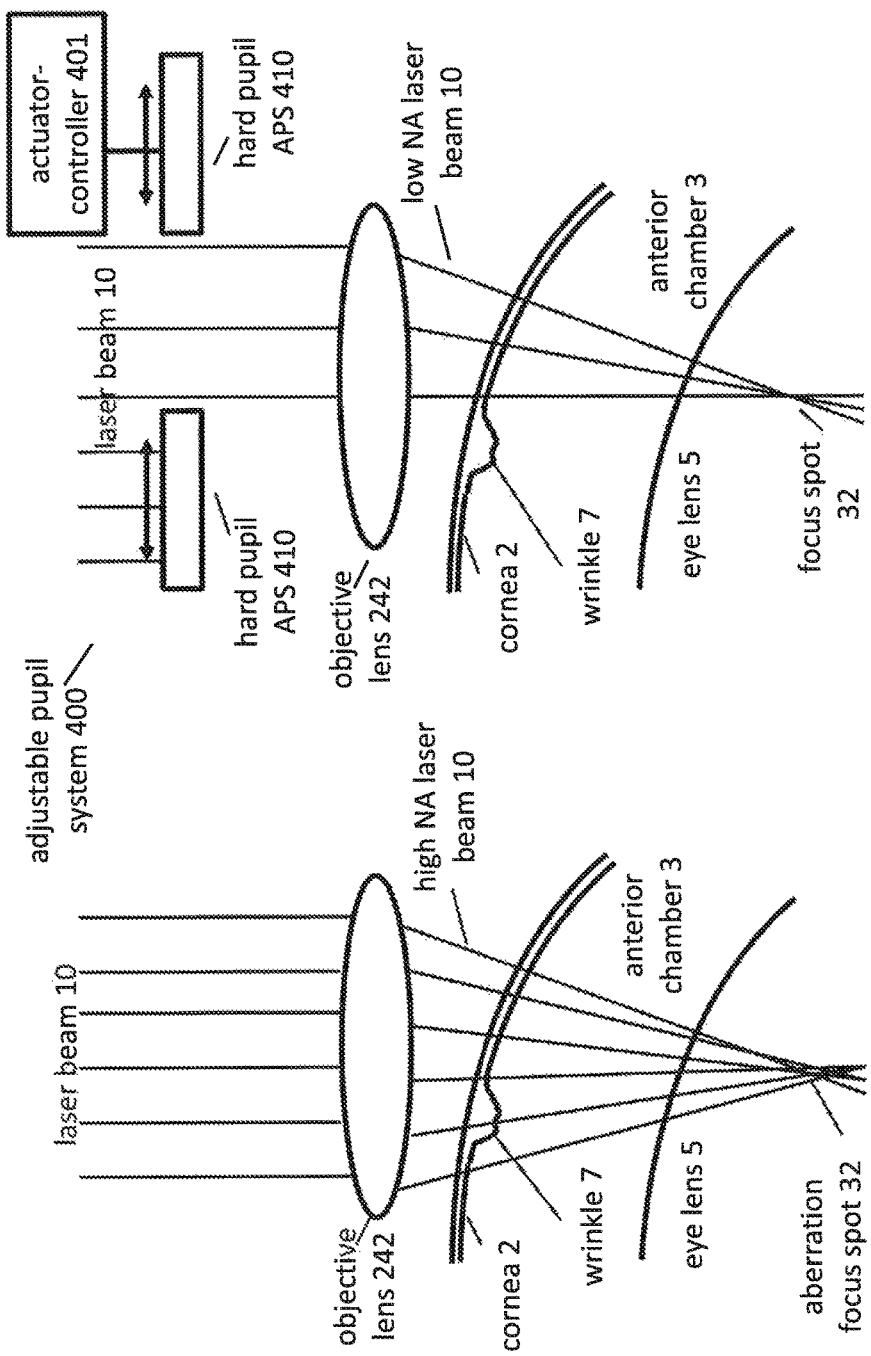
FIGS. 12A-B illustrate a reduction of a numerical aperture of the laser beam with an embodiment of a hard pupil system.

FIGS. 12A-B illustrate that in some embodiments the APS 400 can include a movable or adjustable hard pupil APS 410 or hard pupil system 410. In detail, FIG. 12A illustrates that, when propagating through the scanning delivery system 200, the laser beam 10 can pass through an objective lens 242 inside the objective 240. The objective lens 242 can form a high numerical aperture (high NA) laser beam by focusing the laser beam 10 to the focus spot 32. If there is a defect in a portion of the cross section of the laser beam, such as a wrinkle 7, the phases of some beam components can get distorted, leading to a smearing of the focus spot into an enlarged or aberration focus spot 32.

FIG. 12B illustrates that some embodiments of the surgical laser system 100 can overcome this smearing of the focus spot 32 by including a APS 400 with an adjustable hard pupil APS 410 in the beam path. The location and size of the hard pupil APS 410 can be adjusted so that the hard pupil APS 410 can block the beam components that would have propagated through the defect or wrinkle 7 and would have had their phases distorted. The adjustment can be executed either by an operator of the surgical laser system 100, such as the surgeon, or a computerized actuator-controller 401. The phases of the beam components not blocked by the adjustable hard pupil APS 410 are not distorted, and therefore these beam components intersect each other at the focus spot 32 without smearing out the focus spot. Therefore, this embodiment of the hard pupil APS 410 can reduce the beam distortions by restricting the beam to only those beam components which arrive to the focus spot with their phase undistorted by the wrinkle 7. This restriction of the beam components modulates the phase of the overall laser beam 10, making the hard pupil APS 410 a phase modulating embodiment of the spatio-temporal modulator STM 300. It is noted that the hard pupil APS 410 also narrows a beam convergence cone, thus reducing its numerical aperture NA and tilts its angle relative to the optical axis. The relative or apparent angle of the laser beam is sometimes referred to as its parallax.

In the case of an extended distortive region, the beam distortions can be reduced by adjusting the hard pupil APS 410 to restrict the beam to those beam components which experience only a limited distortion, while blocking the beam components that experience greater distortions by the extended distortive region.

As shown in the above example, embodiments of the scanning delivery system 200, including the objective 240, can be configured to generate the unblocked laser beam 10 with a high numerical aperture (NA), while the hard pupil APS 410 can be configured to transform the high numerical aperture laser beam into a low numerical aperture laser beam 10 by blocking a fraction of the beam components. In some embodiments, the scanning delivery system 200 and its objective 240 can be configured to generate the laser beam with a numerical aperture greater than 0.25, and the hard pupil APS 410 can be configured to reduce the numerical aperture by at least 20%.

The reduction of the initially high numerical aperture of the laser beam by the adjustable pupil system 400 is a general property of the implementations of the adjustable pupil system 400, including the later-described soft pupil APS 420 as well.

In the above implementations, the focus spot can remain essentially in the same depth when the high NA beam is restricted into a low NA beam by the APS 400. In some other embodiments, however, this feature can be utilized to extend the functionality of the surgical laser system 100 by configuring the surgical laser system 100 to perform a corneal procedure when the scanning delivery system 200 is configured to generate the laser beam with the high numerical aperture, and configuring the surgical laser system 100 to perform a cataract procedure when the scanning delivery system 200 is configured to generate the laser beam with the low numerical aperture.

In some implementations, the laser beam 10 can be oversized, i.e. it can have a beam energy and a beam diameter greater than needed for the surgical application. In such implementations, the hard pupil APS 410 can reduce the beam energy and beam diameter to values suitable for the surgical applications.

FIGS. 13A-F illustrate various embodiments of the hard pupil APS 410.

FIG. 13A illustrates that some embodiments of the hard pupil APS 410 can include a rotatable wheel 411 with a pupil or aperture 412, that can rotate around an axis 413. As the wheel 411 turns, the location of the pupil 412 moves around a circle, varying the location of the pupil 412. This implementation of the hard pupil APS 410 varies the selected or unblocked beam components in a modulation time Δt, related to the period of rotation of the wheel 411.

FIG. 13B illustrates that the hard pupil APS 410 can be implemented as a reflective surface 414 on the rotatable wheel 411. Clearly, only those beam components are selected by this embodiment of the hard pupil APS 410 that are reflected by the reflective surface 414.

FIG. 13C illustrates another embodiment of the hard pupil APS 410 that can be implemented in a reflective, transmissive, or absorptive mode. The hard pupil APS 410 can include an array 415 of electronically controllable electro-optical beam modulators. An example is an array 415 of variable transparency LCD pixels 416, controlled by the actuator-controller 401. In a transmissive implementation, the hard pupil APS 410 can be implemented by the actuator-controller 401 controlling a set of the LCD pixels 416 to turn transparent to let a set of selected beam components through, while the non-transparent LCD pixels 416 can block the remaining non-selected beam components, making the LCD array 415 to act as a hard pupil.

FIG. 13D illustrates an embodiment of hard pupil APS 410 that includes a reflector array 417, constructed of adjustable and rotatable micro-reflectors 418. FIG. 13E illustrates that in a reflective implementation, the beam components that fall on rotated micro-reflectors 418 are reflected away from the main optical path, whereas the beam components that fall on non-rotated micro-reflectors 418 are reflected back in an ordered manner and can be redirected by a beam splitter to the subsequent optical elements. Since the non-rotated micro-reflectors 418 reflect the incident beam components only in a narrowed region of the beam 10, they constitute a hard pupil. It is noted here that the inverse implementation, where the rotated micro-reflectors 418 constitute the pupil, faces the difficulty of the beam components acquiring phase factors depending on their location, thus possibly undermining their constructive interference. In operation, the actuator-controller 401 can rotate a set of the micro-reflectors 418 to reflect a set of selected beam components out of the laser beam 10, while the non-activated and non-rotated micro-reflectors 418 reflect the beam components incident on them in an ordered manner, making the reflector array 417 to act as a hard pupil APS 410.

FIG. 13F illustrates that an implementation where the individual micro-reflectors 418 are rotated by small random angles constitutes an embodiment of the spatio-temporal modulator 300, as the rotation makes the beam components reflected from different micro-reflectors 418 arrive to the focus spot 32 with different aberrations or phase factors, in effect having their phases randomized.

During the operation of the above implementations of the hard pupil APS 410, since the location of the focus spot 32 is not impacted by varying the hard pupil, the above described implementations of the hard pupil APS 410 can vary the numerical aperture (NA) of the scanning beam without disturbing the scanning beam in following the scan-pattern. Therefore, in the case of a localized defect, including the adjustable pupil system 400 e.g. in its hard pupil APS 410 implementation into the surgical laser system 100 allows reducing the aperture of the scanning beam so that the scanning beam avoids propagating through the defect region and acquiring a phase distortion, while preserving the laser beam's ability to follow its planned scan-pattern. In the more general case of the presence of non-local corneal wrinkles 7, repeatedly adjusting the aperture in modulation times Δt e.g. by the controller 401 makes the hard pupil APS 410 an implementation of the spatio-temporal modulator STM 300 as well. As such, the hard pupil APS 410 can break up and reduce the large non-cut regions into much smaller ones, as illustrated in FIGS. 6-7. The hard pupil APS 410 can also reduce aberrations, astigmatism and coma of the beam 10, especially in the peripheral regions.

FIGS. 14A-F illustrate implementations of the adjustable pupil system 400 that include a soft pupil APS 420, or soft pupil system 420. The soft pupil APS 420 can include one or more adjustable mirrors or deflectors.

Figure 14A:
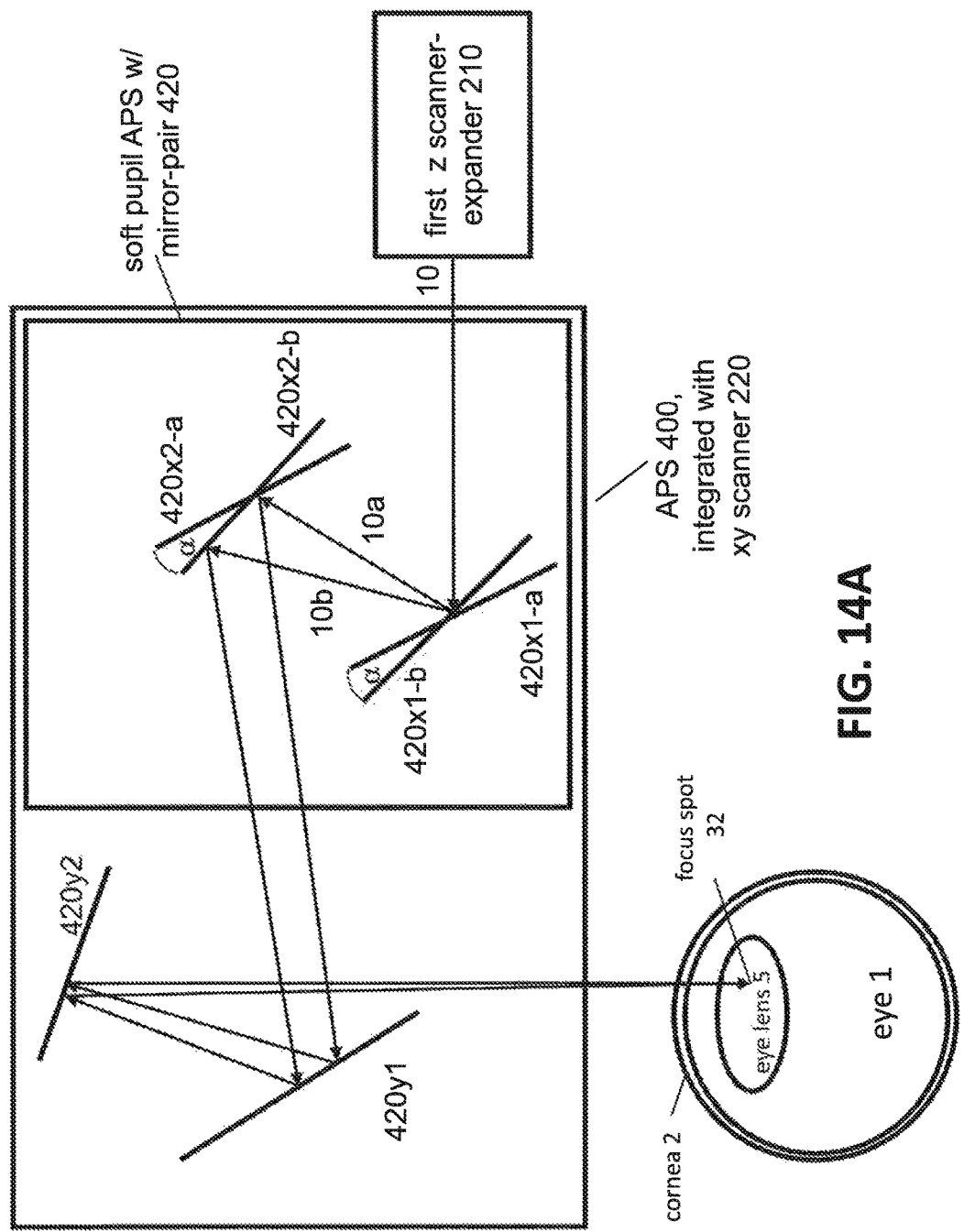
FIGS. 14A-C illustrate a soft pupil system with adjustable beam deflectors.

FIG. 14A illustrates an implementation where the soft pupil APS 420 is integrated into the xy scanner 220. Simple implementations of the xy scanner 220 can involve two mirrors, one to scan the laser beam in the x direction and one in the y direction. However, such implementations can give rise to an excessive amount of aberrations. This can be appreciated by using the concept of a pivot point. A pivot point of a scanning optical element can be defined as the point through which essentially all rays go through, having exited the optical scanning element. This notion is the analogue or extension of the focal point of non-moving refractive elements.

Using this terminology, the pivot point of a one-mirror x scanner is fixed on the x scanning mirror itself. Therefore, the outputted x-scanned beam appears for the subsequent y-scanner as having emanated from a single pivot point in the x plane on the x scanning mirror, and thus propagating into a wide range of angles during scanning. These x-scanned beams, propagating into different angles, are incident on the y scanning mirror at different locations. As the y scanning mirror itself is scanned, the beam has a pivot point in the y plane on the y mirror. Since the x and y mirrors are physically separated, the pivot points in the x and y planes are in different locations. Therefore, the scanned beam will be reflected into a wide range of spatial angles with an asymmetry with respect to the scanning direction, in effect generating a beam whose divergence properties and thus aberrations vary considerably during the xy scanning, degrading the performance and control of the procedure.

Some implementations of the xy scanner 220 can offer an improvement in this aspect: they can include two mirror-pairs for the two scanning functions of the xy scanner 220. Mirrors 420x1 and 420x2 can be a mirror pair that can control the scanning of the laser beam 10 in the x direction. Such a mirror-pair design can lift the x pivot point of the x scanner from the x scanning mirror itself and move it to a suitably chosen point. In some embodiments, the x pivot point can be moved onto the y scanning mirror itself, or to the entrance pupil of the next optical element, in yet others to the target region. In these embodiments, the x-scanned beams propagate to the same point on the y scanning mirror or on the target, essentially eliminating the beam aberrations caused by the divergence of the x-scanned beams of the previous one x-scanning minor design.

In addition, using a mirror-pair 420y1 and 420y2 for the y scanner as well allows moving the y pivot point of the y scanner off the y scanning mirror either to the entrance pupil of the next optical element or to the target region itself. In some embodiments, the pivot point of the x scanner can be moved to either of these places as well.

This is demonstrated in FIG. 14A, where the beam 10 hits the same focus spot 32 when the x scanner mirrors are in the "a" orientation (420x1-a, 420x2-a) and when they are in the "b" orientation (420x1-b, 420x2-b), rotated by an angle α from the "a" orientation. The focus spot 32 remains analogously unmoved when the y scanner mirrors are rotated or reoriented.

Figures 14B, 14C:
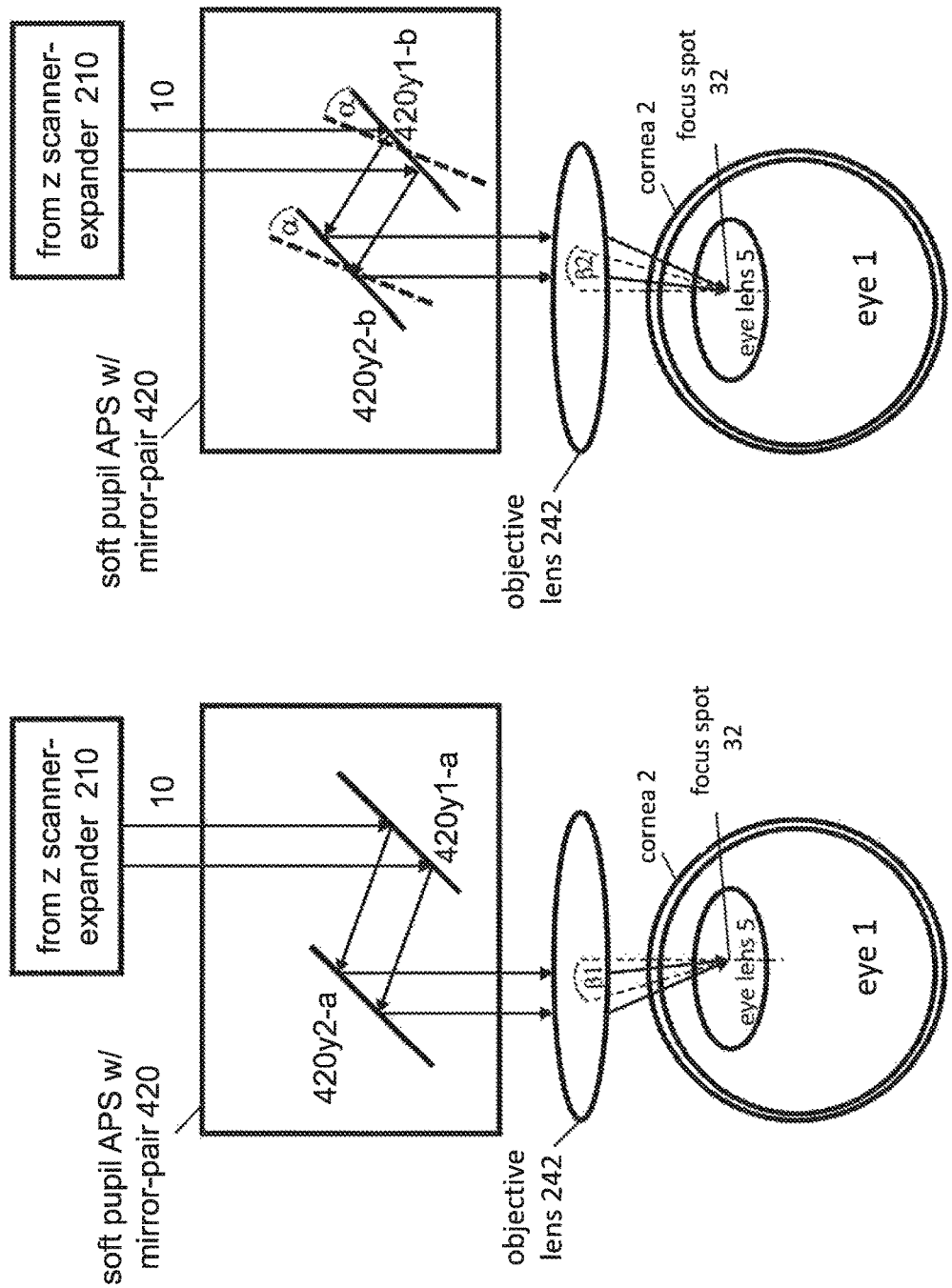

FIGS. 14B-C illustrate the operation of the soft pupil APS 420 in a one mirror-pair implementation in more detail that can be either integrated with the xy scanner 220 or can be implemented anywhere else along the optical beam path. Here, the two lines represent two beam components that intersect in the focus spot 32 when the y scanner mirror-pair (420y1, 420y2) is in the "a" orientation (420y1-a, 420y2-a), and also when it is in the "b" orientation (420y1-b, 420y2-b), rotated by an angle α relative to the "a" orientation. Visibly, because of the movable pivot of the mirror-pair implementation, even after the rotation, the focus spot 32 remained unchanged in the same location. What has changed by the rotation of the mirror-pair (420y1, 420y2) is the apparent angle β, or parallax of the beam, viewed from the target. The concept of the parallax has been already mentioned in the context of the adjustment of the hard pupil APS 410 also changing the parallax of the beam. Demonstrating on a beam-centerline, the parallax changed from β1 to β2 by the rotation of the mirror-pair (420y1, 420y2) from the orientation "a" to "b". Implementations with one minor-pair can move or tilt the parallax in at least one direction, whereas implementations with two mirror-pairs can move or tilt the parallax in both directions when rotating the mirrors of the mirror-pair in a coordinated manner.

Since in the two mirror-pair implementation the pivot points of the x scanner and the y scanner can be moved away from the corresponding mirrors, the xy scanner 220 can control essentially independently (i) the apparent angle β, or parallax, between the scanning beam 10 and an optical axis of the surgical laser system 100, and (ii) a location or scanning path of the focus spot 32. Because of the approximate independence of these controls, the two-mirror-pair implementation of the soft pupil APS 420 can vary the parallax of the beam in two directions without disturbing the focus spot 32 scanning along the originally planned scan-pattern.

Figures 14D, 14E:
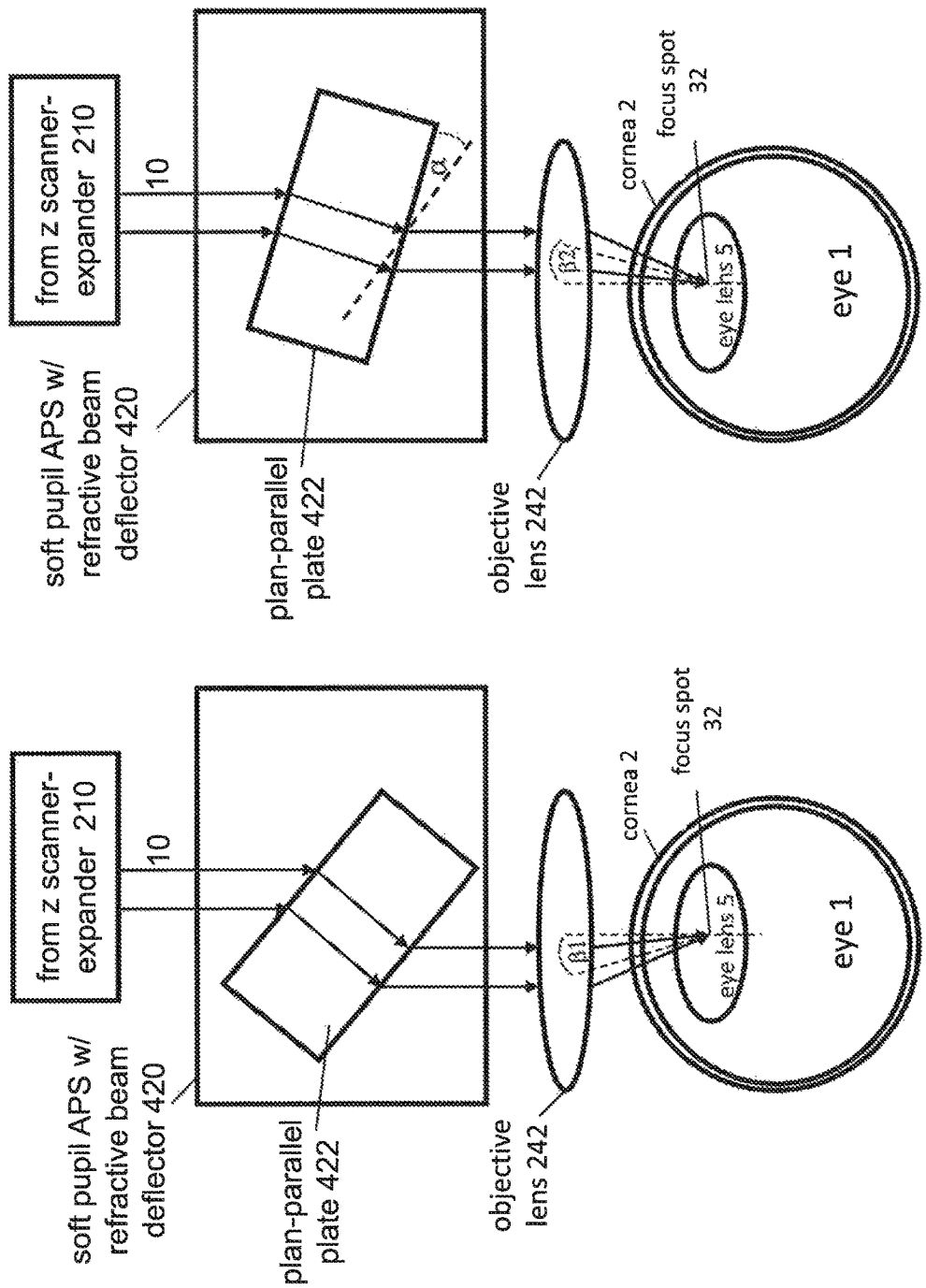

FIGS. 14D-E illustrate that some implementations of the adjustable soft pupil system 420 can include a beam deflector 422 that includes refractive optical elements, such as one or more prisms or plan-parallel plates to execute the function of the rotatable mirror pair. FIGS. 14D-E illustrate a rotatable plan-parallel plate beam deflector 422 where a rotation of the plate translates the beam 10 laterally, thereby changing its parallax β.

Expressing this feature more generally and quantitatively, some implementations of the adjustable pupil system 400 can be configured to adjust at least one of the location of the pupil, the size of the pupil, the beam numerical aperture, the beam convergence cone and the parallax of the laser beam 10 by more than 20% while moving the focus spot 32 by less than the beam diameter at the focus spot. Here, the adjusting has been expressed in relative terms. For example, the location of the pupil can be adjusted by changing the distance of the center of the hard pupil APS 410 or soft pupil APS 420 from the optical axis by more than 20% while moving the focus spot 32 by less than the beam diameter at the focus spot.

In the case of a localized defect, this functionality allows tilting or adjusting the parallax of the scanning beam 10 so that the scanning beam 10 avoids propagating through the localized defect and acquiring a phase distortion. In the more general case of extended corneal wrinkles 7, periodically adjusting the parallax in modulation times Δt can make the two mirror-pair soft pupil APS 420 another implementation of the spatio-temporal modulator STM 300. As such, just like the hard pupil APS 410, the soft pupil APS 420 can break up and reduce large non-cut regions into much smaller ones, as illustrated in FIGS. 6-7. The soft pupil APS 420 can also reduce aberrations, astigmatism and coma of the beam 10, especially in the peripheral regions.

Figures 14F, 14G:
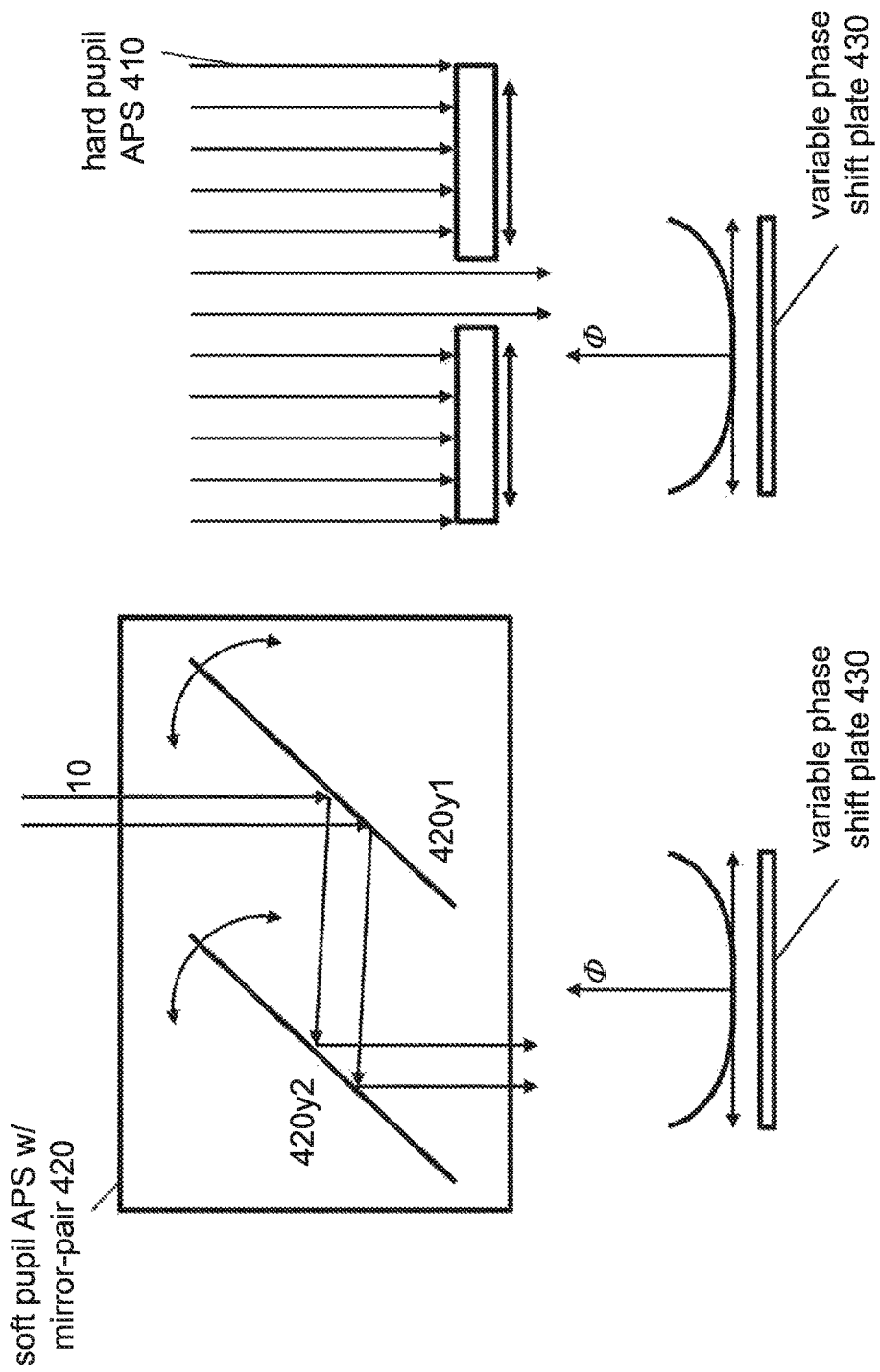

FIGS. 14F-G illustrate another embodiment. Here the surgical laser system 100 can include a variable phase shift plate 430. The curve shows that the variable phase shift plate 430 can be constructed such that a phase shift $\Phi_{plate}$, caused by the beam propagating through a portion of the variable phase shift plate 430 at different locations acquires different but known $\Phi_{plate}$ phase shifts. Therefore, if it is known with some accuracy how much aberration shift $\Phi_{aberration}$ is caused by the corneal wrinkles 7 or other sources of distortion, then the laser beam 10 can be directed with either the soft pupil APS 420 (FIG. 14F) or the hard pupil APS 410 (FIG. 14G) to that part of the variable phase shift plate 430 that introduces the phase shift $\Phi_{plate}$ that provides the best compensation for the aberration shift $\Phi_{aberration}$ to minimize the total phase shift of the beam components:

$$\Phi_{total} = \Phi_{aberration} + \Phi_{plate}.$$

Referring back to FIGS. 10-14, some systems can have a combination of a hard pupil APS 410 and a soft pupil APS 420 for enhanced functionalities.

Yet other implementations can include the adjustable pupil system 400 and a spatio-temporal modulator (STM) 300, or space-time modulator 300 that is configured not to modulate a pupil of the laser system 100. Embodiments of such spatio-temporal modulators 300 can include rotatable wheels with corrugated surfaces, electro-optical modulator arrays, LCD pixel arrays, acousto-optical phase modulators, deformable reflectors and amplitude modulators.

In some implementations the APS 400 can be adjusted without receiving a control or feedback signal from a beam diagnostic system, a wavefront analyzer or an imaging system of the surgical laser system 100. Even without such beam diagnostic or imaging systems, these implementations can introduce a spatio-temporal modulation of the phase of the beam and thus randomize the phase of the laser beam 10 to break up, reduce or even eliminate the no-cut regions. Further, these no-feedback systems can reduce the complexity of the surgical laser system 100 and speed up its operations.

Some of these APS 400 systems can include the actuator-controller 401. The pupil can be adjusted under the control of this controller 401. In the phase-randomizer implementations, the controller 401 can adjust the pupil in a modulation time Δt repeatedly or periodically. The periodic adjustment can take place with a high frequency i.e. with short modulation times that can be set by the inverse of the pulse repetition rate, the scanning line return time or the scan segment return time, as described in relation to FIGS. 9A-C.

In the specific example of the hard pupil APS 410 implementation of FIG. 13A, the modulation time Δt can be approximately the repetition time. During this modulation time the actuator-controller 401 can rotate the wheel 411 by an angle so that the location of the pupil or aperture 412 after Δt can be substantially different from its location before the rotation. Therefore, even if a destructive interference of the phases of the beam components is caused by the corneal wrinkles 7 and prevents the photodisruption of the target tissue by a laser pulse directed to a particular spot of the scan-pattern, the phases of the beam components of the next laser pulse, directed to the neighboring spot, can experience a substantially different interference, and therefore the next pulse very likely will be able to photodisrupt the target region again. For example, the actuator-controller 401 can add a random deflection component to the scanning software of the xy scanner mirrors 420x and 420y of the soft pupil APS 420. Thus, when operated with the actuator-controller 401, the APS 400, hard pupils APS 410 and soft pupil APS 420 can produce the type of spatio-temporal modulation illustrated in FIGS. 6A-C that is sufficient to reduce or eliminate the large uncut regions.

In other implementations the modulation time Δt can be longer. For instance, the adjustment can be carried out only once, after an imaging is performed by the imaging system 120 after a stage of the surgical process has been completed. This adjustment can be carried out by the controller 401 or manually by the surgeon, and can involve adjusting a location or a size of the pupil or the parallax with either the hard pupil APS 410 or the soft pupil APS 420. An example is scanning the laser beam 10 along a circular capsulotomy scan-pattern with a first pupil setting, then imaging the capsulotomy and discovering that a sizeable portion remained uncut, readjusting the pupil to a second setting, followed by rescanning at least a portion of the capsulotomy circle with the second pupil setting that has been scanned with the first pupil setting unsuccessfully. Here, of course the first pupil setting is different from the second pupil setting.

Some implementations can also include an image processor 122 to determine one or more beam distortions from the image generated by the imaging system 120, and to calculate an adjustment of the adjustable pupil system 400 to reduce at least one of the determined beam distortions. These implementations can also include the actuator-controller 401, coupled to the image processor 122 to adjust the pupil according to the adjustment calculated by the image processor 122. Once the actuator-controller 401 adjusts the pupil, the scanning of the beam 10 can continue, resume, or get repeated, typically photodisrupting the target region with improved efficiency. As earlier, the imaging system 120 can image the target region before or after the surgical procedure.

In an example, the imaging system 120 can image the eye 1 after a capsulotomy. The image processor 122 can analyze the image and may determine that a portion of a capsulotomy was inefficient, leaving behind an uncut tag. The image processor 122 may also analyze the image of the cornea and can find that a region of the cornea is strongly wrinkled, probably causing the uncut tag. The image processor 122 can then calculate what is the necessary shift or the hard pupil in a hard pupil APS 410, or the necessary tilt of the parallax in a soft pupil APS 420 to adjust the laser beam to avoid the strongly wrinkled portion of the cornea. The image processor 122 can then send a feedback or control signal to the actuator-controller 401 with the recommended adjustments. In response, the actuator-controller 401 may prompt the adjustable pupil system 400 to either shift the location of the hard pupil APS 410 or tilt the parallax of the soft pupil APS 420 to implement the recommended changes. In cases when the distorting defects are not localized, the analysis of how to reduce the beam distortions can be more complex.

Many of the above implementations included the imaging system 120 and the actuator-controller 401, and utilized their coordinated operation to improve the efficiency of the photodisruption. These implementations offer numerous enhanced functionalities and improved precision. However, their system is more complex and their operation consumes precious surgical time. For this reason, another class of implementations does not incorporate the image processor 122 and the actuator-controller 401. In these implementations, the adjustable pupil system 400 can be adjustable manually. An example is a manually adjustable soft pupil APS 420 in a surgical laser system 100 that also includes the in-depth imaging system 120. The surgeon may dock the patient interface 20 on the eye 1, then image the eye 1 with the in-depth imaging system 120 and identify a localized wrinkle 7 of the cornea 2. Once the location of the wrinkle 7 is determined, the surgeon can manually adjust the parallax of the laser beam 10 by adjusting the soft pupil APS 420 so that the laser beam 10 avoids propagating through the localized corneal wrinkle 7 during the scanning along the scan-pattern. Such a manual implementation can also improve the efficiency of the photodisruption and can do so with a less complex system.

Figure 15:
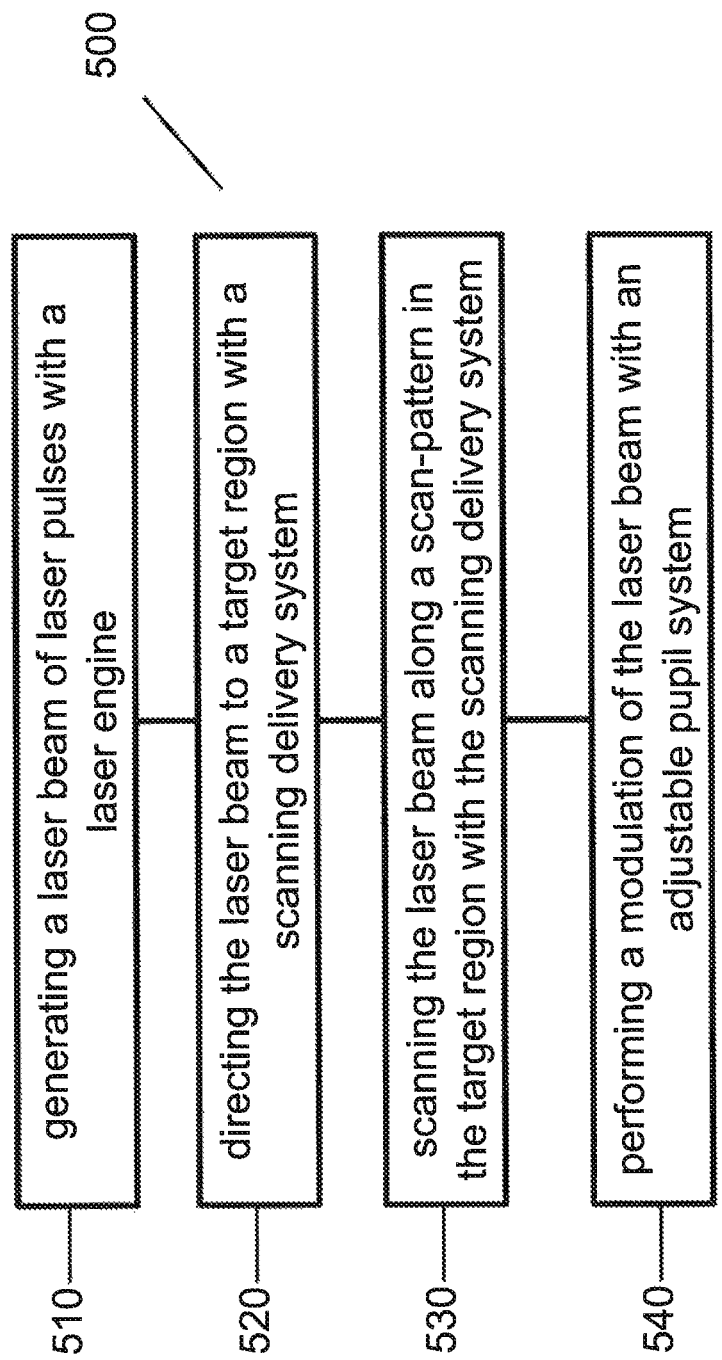
FIG. 15 illustrates a method of using an adjustable pupil system.

FIG. 15 illustrates a method 500 of adjusting a pupil of a laser beam, the method including a generating 510 of a laser beam of laser pulses with a laser engine; a directing 520 of the laser beam to a target region with a scanning delivery system; a scanning 530 of the laser beam along a scan-pattern in the target region with the scanning delivery system; and a performing 540 of a modulation of the laser beam with an adjustable pupil system.

In some implementations of the method 500, the performing 540 can include varying at least one of a size and a location of a hard pupil of the laser beam. In some other implementations, the performing 540 can include varying a parallax of the laser beam by adjusting a soft pupil APS.

The performing 540 of the pupil modulation can be performed within a modulation time Δt less than 10 times an repetition time of the laser pulses, or less than a return time of the scan-pattern, wherein the scan-pattern can include a set of closely spaced lines or a set of closely spaced scan segments, and the return time is a time the scan of the laser beam takes between passing a first point on a first scan line or scan segment and a second point on a second scan line or scan segment nearest to the first point.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

What is claimed is:

1. A surgical laser system, comprising:
a laser engine, configured to generate a laser beam of laser pulses;
a scanning delivery system, comprising a z-scanner, an xy-scanner, and an objective, the scanning delivery system configured
to direct the laser beam to a target region, and
to scan the laser beam along a scan-pattern in the target region;
an imaging system, configured to image a portion of the target region at least one of before a surgical cut and after a surgical cut;
a rotatable wheel positioned along an optical path of the laser beam, the rotatable wheel comprising an axis of rotation and a pupil, wherein the pupil is offset from the axis of rotation; and
a computer-controlled actuator configured to rotate the rotatable wheel about the axis of rotation while the laser beam is scanned such that a first portion of the laser beam impinges on the pupil at a first rotatable wheel angle and a second portion of the laser beam impinges on the pupil at a second rotatable wheel angle;
wherein the pupil comprises at least one of an aperture and a reflector.

2. The surgical laser system of claim 1, wherein:
computer-controlled actuator is configured to rotate the rotatable wheel to reduce a length of an un-photo-disrupted scan-segment left behind when the laser beam is scanned through a distorted region of the target region by a factor of more than 2 compared to the length of an un-photo-disrupted scan-segment left behind when the same surgical laser system is scanned through the same target region but without the adjustable pupil system.

3. The surgical laser system of claim 1, wherein:
the computer-controlled actuator is configured to rotate the rotatable wheel to adjust a location of the pupil within a modulation time less than 10 times a pulse repetition time of the laser pulses.

4. The surgical laser system of claim 1, wherein:
the pupil is one of a transmissive pupil, an absorptive pupil and a reflective pupil.

5. The surgical laser system of claim 1, wherein:
the computer-controlled actuator is configured to rotate the rotatable wheel to perform a space and time dependent phase modulation of the laser beam with a maximum phase modulation of at least $\pi/4$.

6. The surgical laser system of claim 1, wherein:
the computer-controlled actuator is configured rotate the rotatable wheel to randomize a phase of beam components of the laser beam on a modulation length and a modulation time.

7. The surgical laser system of claim 1, wherein:
the scanning delivery system is configured to generate the laser beam with a numerical aperture in the range of 0.15-0.45; and
the computer-controlled actuator is configured to rotate the rotatable wheel to reduce the numerical aperture of the laser beam by at least 20%.

8. The surgical laser system of claim 1, wherein:
the computer-controlled actuator is configured to rotate the rotatable wheel to change a parallax of the laser beam.

9. The surgical laser system of claim 1, wherein:
the computer-controlled actuator is configured to rotate the rotatable wheel to adjust at least one of a numerical aperture, a beam convergence cone, and a parallax of the laser beam by more than 20% while moving the focus spot by less than a beam diameter at the focus spot.

10. The surgical laser system of claim 1, comprising:
an image processor, configured
to determine one or more beam distortions from the image generated by the imaging system, and
to calculate an adjustment of the actuation of the rotatable wheel to reduce at least one of the determined beam distortions; and
a computerized actuator-controller, coupled to the image processor and configured to cause the computer-controlled actuator to adjust the rotation of the rotatable wheel according to the adjustment calculated by the image processor.

11. The surgical laser system of claim 1, wherein:
the scanning delivery system is configured to rescan the laser beam with a second pupil setting tracking a portion of the scan-pattern that has been previously scanned with a first pupil setting, wherein
the first pupil setting is different from the second pupil setting.

* * * * *